(12) United States Patent
Noergaard et al.

(10) Patent No.: US 6,834,237 B2
(45) Date of Patent: Dec. 21, 2004

(54) METHOD AND SYSTEM FOR CLASSIFYING A BIOLOGICAL SAMPLE

(75) Inventors: Lars Noergaard, Hellerup (DK); Morten Albrechtsen, Charlottenlund (DK); Ole Ingemann Olsen, Charlottenlund (DK); Niels Harrit, Copenhagen NV (DK); Rasmus Bro-Joergensen, Koege (DK)

(73) Assignee: Medicometrics APS, Charlottenlund (DK)

( * ) Notice: Subject to any disclaimer, the term of this patent is extended or adjusted under 35 U.S.C. 154(b) by 0 days.

(21) Appl. No.: 10/297,187

(22) PCT Filed: Jun. 1, 2001

(86) PCT No.: PCT/DK01/00383

§ 371 (c)(1),
(2), (4) Date: Apr. 16, 2003

(87) PCT Pub. No.: WO01/92859

PCT Pub. Date: Dec. 6, 2001

(65) Prior Publication Data

US 2003/0162301 A1 Aug. 28, 2003

(30) Foreign Application Priority Data

Jun. 2, 2000 (DK) .................................... PA 2000-00863

(51) Int. Cl.[7] ............................ G01N 21/64; A61B 5/00
(52) U.S. Cl. ...................................................... 702/19
(58) Field of Search .................. 702/19; 250/341.1, 250/339.07, 363.01; 356/39

(56) References Cited

U.S. PATENT DOCUMENTS

| 4,782,234 A | 11/1988 | Chudyk et al. |
|---|---|---|
| 5,182,214 A | 1/1993 | Kessler et al. |
| 5,196,709 A | 3/1993 | Berndt et al. |
| 5,491,344 A | 2/1996 | Kenny et al. |
| 5,528,368 A | 6/1996 | Lewis et al. |

(List continued on next page.)

FOREIGN PATENT DOCUMENTS

| EP | 0 644 412 | 3/1995 |
|---|---|---|
| WO | WO 96/30746 | 10/1996 |
| WO | WO 9630746 | * 10/1996 |
| WO | WO 98/24369 | 6/1998 |
| WO | WO 9824369 | * 6/1998 |
| WO | WO 00/42907 | 7/2000 |

OTHER PUBLICATIONS

K.M. O'Brien et al., "Development and evaluation of spectral classification algorithms for fluorescence guided laser angioplasty", IEEE Transactions on Biomedical Engineering, vol. 36, No. 4, Apr. 1989, pp. 424–443.*

(List continued on next page.)

Primary Examiner—Donald McElheny, Jr.
(74) Attorney, Agent, or Firm—Merchant & Gould, P.C.

(57) ABSTRACT

The present invention relates to a method of training a classification system for characterising a biological sample, a diagnostic classification system, as well as a method of characterising a condition in an animal or a human being by using parameters obtained from the sample. The invention relates to classification based on physical parameters obtained from luminescence spectroscopy on light emitted from the sample. The data obtained from a spectrofluorimetric analysis can be considered a finger-print of the sample. Each sample gives rise to a unique spectrofluorometric set of physical parameters. By analysing the fluorescence data, it is possible to classify samples into two or more classes based on the fluorescence spectra, such as classifying with respect to presence/abs of a specific disease, group of diseases or risk of later attaining a specific disease or a body condition, or concentration of a specific compound or medicine.

60 Claims, 35 Drawing Sheets

U.S. PATENT DOCUMENTS

Figure 1:
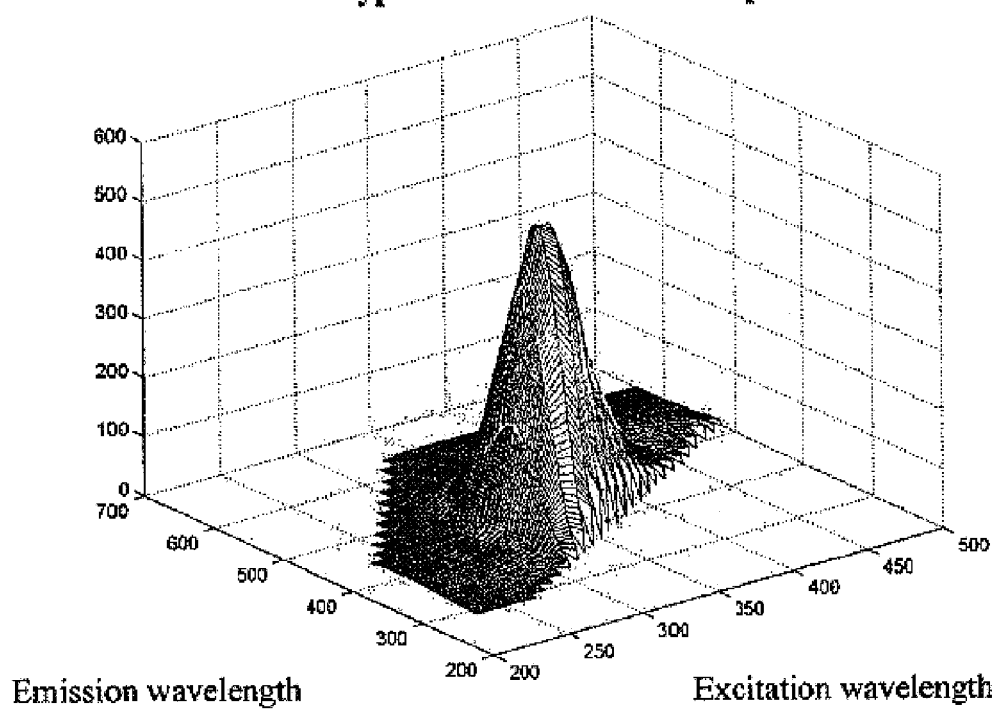

| | | | |
|---|---|---|---|
| 5,548,124 A | | 8/1996 | Takeshima et al. |
| 5,557,415 A | | 9/1996 | Nielsen et al. |
| 5,576,544 A | * | 11/1996 | Rosenthal ............... 250/341.1 |
| 5,605,838 A | | 2/1997 | Backhaus et al. |
| 5,734,587 A | | 3/1998 | Backhaus et al. |
| 5,865,754 A | | 2/1999 | Sevick-Muraca et al. |
| 5,869,001 A | | 2/1999 | Backhaus et al. |
| 5,946,083 A | | 8/1999 | Melendez et al. |
| 5,955,737 A | | 9/1999 | Hallidy et al. |
| 5,968,731 A | | 10/1999 | Layne et al. |
| 5,976,466 A | | 11/1999 | Ratner et al. |
| 5,983,251 A | | 11/1999 | Martens et al. |
| 5,999,844 A | | 12/1999 | Gombrich et al. |
| 6,002,476 A | | 12/1999 | Treado |
| 6,014,904 A | | 1/2000 | Lock |
| 6,025,149 A | | 2/2000 | Cuckle et al. |

OTHER PUBLICATIONS

Lars Munck, Kjemometri og samfunn, © Redaksjonsgruppen 1996, 510–521.

Rasmus Bro, "Exploratory study of sugar production using fluorescence spectroscopy and multi–way analysis", Chemometrics & Intelligent Laboratory Systems 1998, 2–21.

Leiner et al., Total Luminescence Spectrometry and Its Application in the Biomedical Sciences, in Baeyens et al., Luminescence Techniques in Chemical and Biochemical Analysis, Marcel Dekker, Inc. 1991, 381–419.

Munck et al., Chemometrics in food science—a demonstration of the feasibility of highly exploratory, inductive evaluation strategy of fundamental scientific significance, Chemometrics and Intelligent Laboratory Systems, 44, 31–60, 1998.

Lars Nørgaard, Classification and prediction of quality and process parameters of thick juice and beet sugar by fluorescence spectroscopy and chemometrics, Zuckerind. 120, 970–981, 1995.

O'Brien et al., "Development and evaluation of spectral classification algorithms for fluorescence guided laser angioplasty", IEEE Transactions on Biomedical Engineering 36, 424–430, 1989.

Alsberg BK, Goodacre R, Rowland JJ, Kell DB, Classification of pyrolysis mass spectra by fuzzy multivariate rule induction–comparison with regression, k–nearest neighbour, neural and decision–tree methods, Analytica Chimica Acta, 1997, 348, 389–407.

Bartholomew DJ, The Foundation of factor analysis, Biometrika, 1984, 71, 221–232.

Björkström A, Sundberg R, A generalized view on continuum regression, Scandinavian Journal of Statistics, 1999, 26, 17–30.

Bro R, PARAFAC. Tutorial and applications, Chemom Intell Lab Syst, 1997, 38, 149–171.

Bro R, Multiway calibration. Multi–linear PLS, Journal of Chemometrics, 1996, 10, 47–61.

Bro R, Multi–way Analysis in the Food Industry. Models, Algorithms, and Applications. Ph.D. thesis, University of Amsterdam (NL), 1998, 259–264.

Bro R, Exploratory study of sugar production using fluorescence spectroscopy and multi–way analysis, Chemom Intell Lab Syst, 1999, 46, 133–147.

Cheng B, Titterington DM, Neural Networks: A Review from a Statistical Perspective, Statistical Science, 1994, 9, 2–54.

de Jong S, Kiers HAL, Principal covariates regression. Part 1. Theory, Chemom Intell Lab Syst, 1992, 14, 155–164.

Esbensen K, Wold S. SIMCA, MACUP, SELPLS, GDAM, SPACE & UNFOLD: The way towards regionalized principal components analysis and subconstraiend N–way decomposition—with geological illustrations, Proc Nord Symp Appl Statist, Stavanger, 1983.

Faber NM, Buydens LMC, Kateman G, Generalized rank annihilation method. I: Derivation of eigenvalue problems, Journal of Chemometrics, 1994, 8, 147–154.

Golub GH, Hansen PC, O'leary D, Tikhonov Regularization and Total Least Squares, SIAM Journal of Numerical Analysis, 1999, 21, 185–194.

Grung B, Manne R, Missing values in principal component analysis, *Chemom Intell Lab Syst,* 1998, 42, 125–139.

Indahl UG, Sahni NS, Kirkhus B, Naes T, Multivariate strategies for classification based on NIR–spectra—with application to mayonnaise, Chemom Intell Lab Syst, 1999, 49, 19–31.

Kohonen T, Self–organized formation of topologically correct feature maps, Biological Cybernetics, 1982, 43, 59–69.

Martens H, Naes T, Multivariate calibration. John Wiley & Sons, Chichester, 1989,Martens H, Naes T, Multivariate calibration by data compression, *Near Infrared Technology in the Agricultural and Food Industries,* (Eds. Williams,P and Norris,K), The american association of cereal chemists, Inc., St. Paul, 1987, 57–87.

Naes T, Isaksson T, Some modifications of locally weighted regression (LWR), NIR news, 1994, 5, 8–9.

Rajko R, Treatment of model error in calibration by robust and fuzzy procedures, Analytical Letters, 1994, 27, 215–228.

Wold S, Dunn WJ, III, Multivariate quantitative structure–activity relationships (QSAR): conditions for their applicability, J Chem Inf Comput Sci, 1983, 23, 6–13.

Wold S, Cross–validatory estimation of the number of components in factor and principal components models, Technometrics, 1978, 20, 397–405.

Wold S, Albano C, Dunn WJ, III, Edlund U, Esbensen KH, Geladi P, Hellberg S, Johansson E, Lindberg W, Sjöström M, Multivariate data analysis in chemistry, *Chemometrics. Mathematics and Statistics in Chemistry,* (Ed. Kowalski, BR), D. Reidel Publishing Company, Dordrecht, 1984, 2–79.

* cited by examiner

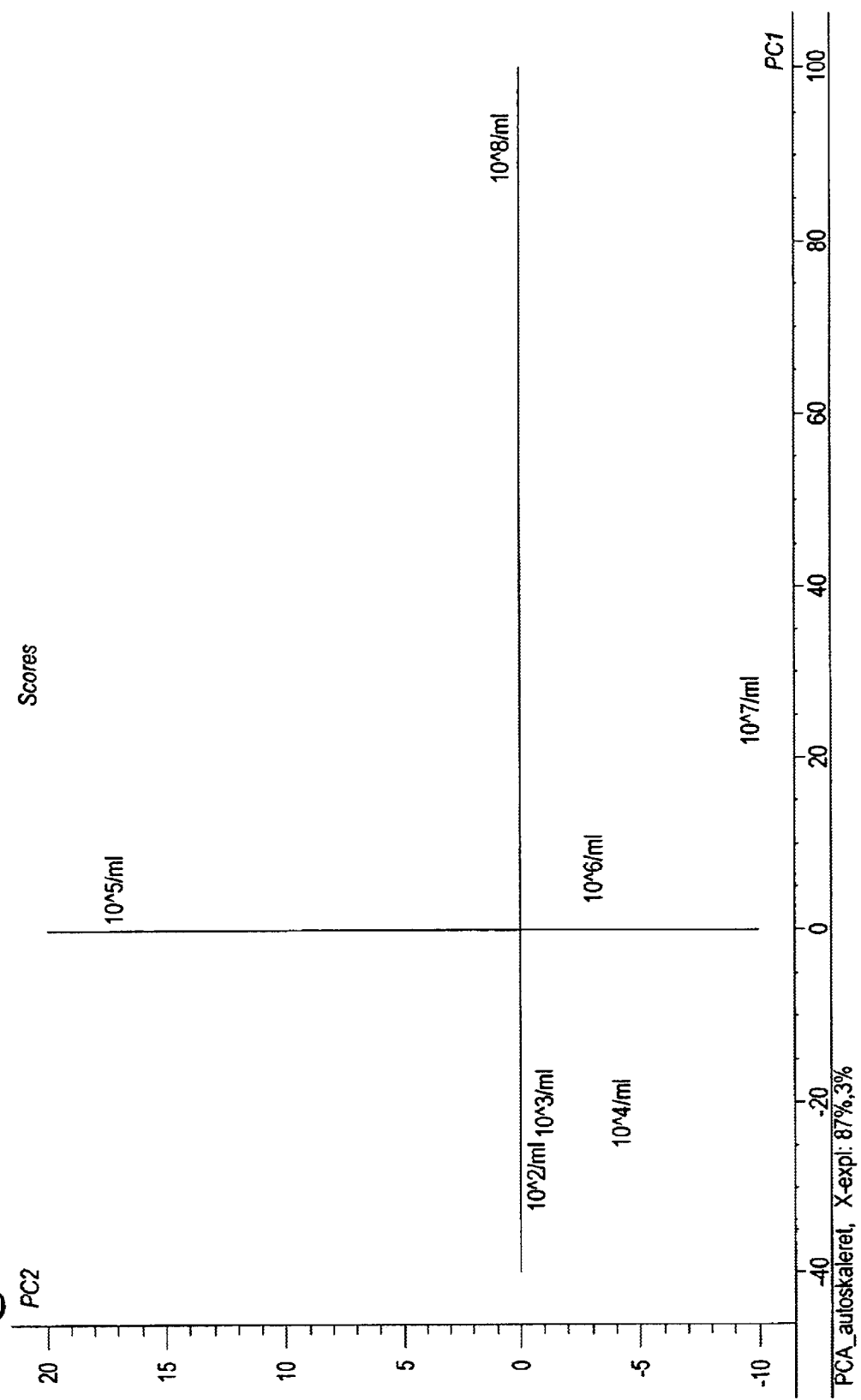

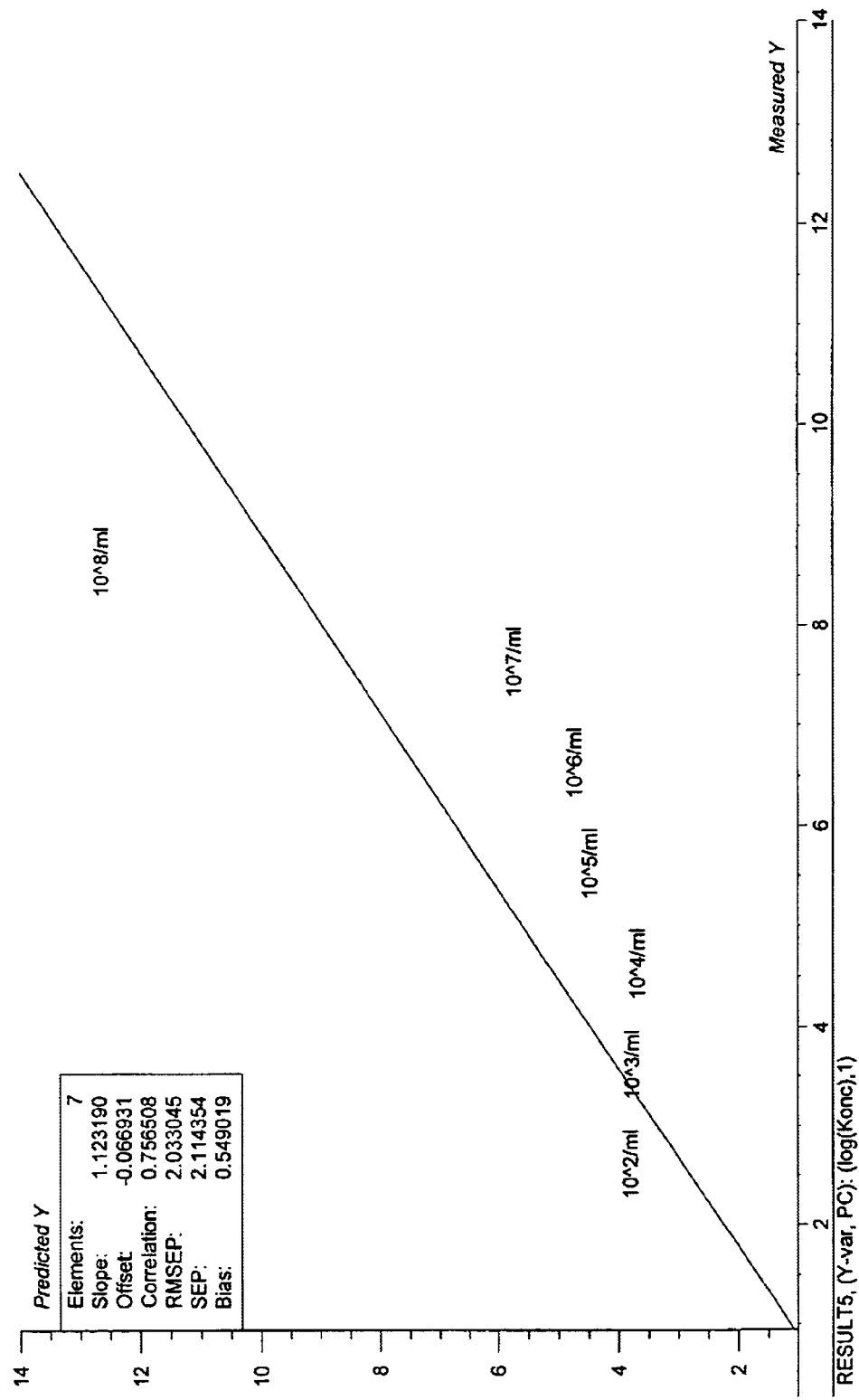

Transmission – Undiluted sample

Transmission – diluted 1:5000

Emission          Excitation

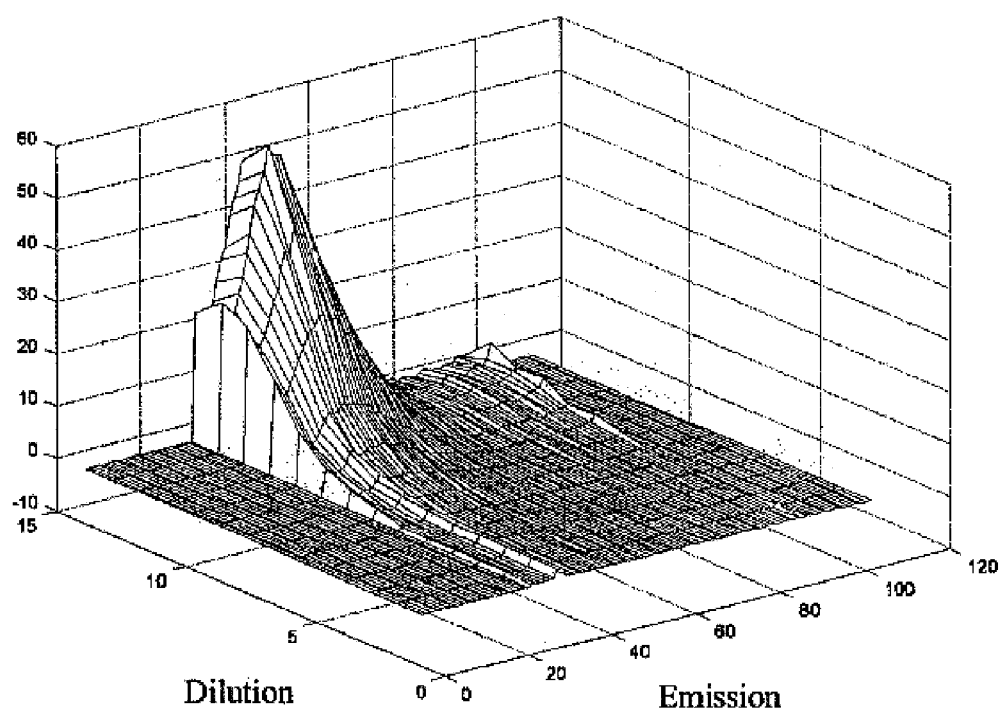
FIG. 19B   Excitation 360 nm

METHOD AND SYSTEM FOR CLASSIFYING A BIOLOGICAL SAMPLE

The present invention relates to a method of training a classification system for characterising a biological sample, a diagnostic classification system, as well as a method of characterising a condition in an animal or a human being by using parameters obtained from the sample.

BACKGROUND

A need for a fast and reliable primary diagnostic tool providing information indicative of a disease or a group of diseases has existed for years.

In U.S. Pat. No. 4,755,684 (Leiner et al.) a method for tumor diagnosis by means of serum tests is disclosed. The method includes excitation of the serum by an excitation radiation at least of a wavelength between 250 nm and 300 nm, and its fluorescence intensity is measured at predetermined emission wavelengths. From deviations of these measuring values, a conclusion may be drawn with respect to the presence of a neoplastic disease. Measurements at one or two excitation wavelengths are suggested. Up to three emission wavelengths are determined for each excitation wavelength and an intensity value is determined. Since very little information from the fluorescence spectroscopy is used the diagnosis is very rough and insecure. Only about 60% are diagnosed correctly and the diagnosis is limited to a yes or no.

In WO 96/30746 and WO 98/24369 fluorescence spectra are used to screen tissue samples in situ, wherein the tissue suspected to be dysplastic tissue is directly subjected to fluorescence spectroscopy. The methods are used to distinguish between dysplastic cervical tissue and normal cervical tissue. In O'Brien K. M. et al "Development and evaluation of spectral classification algorithms for fluorescence guided laser angioplasty", IEEE TRANSACTIONS ON BIOMEDICAL ENGINEERING, vol. 36, No. 4, April 1989, pages 424–4430, fluorescence spectroscopy is used to distinguish normal arterial tissue from atherosclerotic tissue. None of these methods allows a specific diagnosis to be made based on analysis of spectra from tissue or bodufluids not directly related to the diseased tissue.

In U.S. Pat. No. 5,734,587 a method of analyzing sample liquids by generating infrared spectra of dried samples and evaluating using a multivariate evaluation procedure is disclosed. In the evaluation procedure the samples are assigned to classes. The evaluation procedure is trained with samples of known classes to adjust the parameters of the evaluation procedures, such that samples of unknown classification can be assigned to known classes. The samples analysed are clinically relevant liquid samples, that have to be dried before generating the infrared spectra of the samples due to the nature of infrared spectra.

Most organic compounds absorb light in the visible or ultraviolet part of the electro-magnetic spectrum. Many molecules emit the absorbed excitation energy in the form of fluorescence. A fluorescence spectrum is obtained by transmitting light to the sample (excitation light) and determining the spectral distribution of the light emitted from the sample. In the case where only one fluorescent compound is present in a weakly absorbing solution, the spectral profile of the fluorescence will be invariant with respect to the excitation wavelength. Only the intensity of the fluorescence will vary with the wavelength of the excitation light in accordance with the absorption spectrum.

If more than one fluorescent compound is present in the solution the relation between excitation and emission intensities will rapidly increase to a very high level of complexity. The individual compounds will absorb differently for each excitation wavelength, the intensity and distribution of the fluorescence will vary with excitation wavelength, and reabsorption of emitted photons might occur.

When a series of fluorescence spectra using different excitation wavelengths are recorded, the spectra collected represents an emission-excitation-matrix (EEM), which can be displayed as a 3-dimensional landscape (FIG. 1). The EEM is specific for the specific mixture of compounds and the conditions under which it is measured.

SUMMARY

It has been an object of the present invention to provide a method capable of classifying samples with unknown properties in a system not requiring any drying, enrichment, separation or concentration of the sample before determining the class, to which the sample belongs.

This has been possible by subjecting the sample to fluorescence spectroscopy or a variant thereof, whereby liquid as well as solid samples may be classified.

Thus, in a first aspect the present invention relates to a method of training a classification system for characterising a biological sample with respect to at least one condition, comprising
  a) obtaining a biological sample from an animal, including a human, wherein said biological sample is selected from body fluids and/or tissue, wherein the tissue sample is not associated with said condition(s),
  b) obtaining characterisation information related to each biological sample,
  c) exposing the sample to excitation light within a predetermined range of wavelength,
  d) determining physical parameter(s) of light emitted from the sample,
  e) repeating step a) to d) until the physical parameters of all training samples have been determined,
  f) optionally performing a data handling of the obtained physical parameters obtaining data variables,
  g) optionally performing a multivariate data analysis of the data variables obtaining model parameters describing the variation of the data variables,
  h) classifying the biological samples into at least two different classes correlated to the characterisation information, obtaining a trained classification system.

In a preferred embodiment the method comprises the steps of:
  a) obtaining a biological sample from an animal, including a human, wherein said biological sample is selected from body fluids and/or tissue, wherein the tissue sample is not associated with said condition(s),
  b) obtaining characterisation information related to each biological sample,
  c) exposing the sample to excitation light within a predetermined range of wavelength,
  d) determining physical parameter(s) of light emitted from the sample,
  e) repeating step a) to d) until the physical parameters of all training samples have been determined,
  f) performing a data handling of the obtained physical parameters obtaining data variables,
  g) optionally performing a multivariate data analysis of the data variables obtaining model parameters describing the variation of the data variables, h) classifying the biological samples into at least two different classes correlated to the characterisation information, obtaining a trained classification system.

In another preferred embodiment the method comprises the steps of:
a) obtaining a biological sample from an animal, including a human, wherein said biological sample is selected from body fluids and/or tissue, wherein the tissue sample is not associated with said condition(s),
b) obtaining characterisation information related to each biological sample,
c) exposing the sample to excitation light within a predetermined range of wavelength,
d) determining physical parameter(s) of light emitted from the sample,
e) repeating step a) to c) until the physical parameters of all training samples have been determined,
f) performing a data handling of the obtained physical parameters obtaining data variables,
g) performing a multivariate data analysis of the data variables obtaining model parameters describing the variation of the data variables,
h) classifying the biological samples into at least two different classes correlated to the characterisation information, obtaining a trained classification system.

In another aspect the present invention relates to a classification system for characterising a biological sample, said system comprising:
a) a sample domain for comprising a biological sample,
b) light means for exposing the sample to excitation light in the sample domain,
c) a detecting means recording the physical parameter(s) of light emitted from the sample,
d) optionally computing means for performing data handling of the physical parameters, obtaining data variables,
e) optionally processing means for providing model parameters from data variables of the sample,
f) at least one storage means for storing physical parameters and/or data variables and/or model parameters of the biological sample,
g) at least one storage means for storing physical parameters and/or data variables and/or model parameters and characterisation information of a trained classification system,
h) means for correlating physical parameters and/or data variables and/or model parameters from the sample with physical parameters and/or data variables and/or model parameters of the trained system, and
i) means for displaying the characterisation class(es) of a sample.

In a preferred embodiment the system comprises:
a) a sample domain for comprising a biological sample,
b) light means for exposing the sample to excitation light in the sample domain,
c) a detecting means recording the physical parameter(s) of light emitted from the sample,
d) computing means for performing data handling of the physical parameters, obtaining data variables,
e) optionally processing means for providing model parameters from data variables of the sample,
f) at least one storage means for storing physical parameters and/or data variables and/or model parameters of the biological sample,
g) at least one storage means for storing physical parameters and/or data variables and/or model parameters and characterisation information of a trained classification system,
h) means for correlating physical parameters and/or data variables and/or model parameters from the sample with physical parameters and/or data variables and/or model parameters of the trained system, and
i) means for displaying the characterisation class(es) of a sample.

In another preferred embodiment the system comprises:
a) a sample domain for comprising a biological sample,
b) light means for exposing the sample to excitation light in the sample domain,
c) a detecting means recording the physical parameter(s) of light emitted from the sample,
d) computing means for performing data handling of the physical parameters, obtaining data variables,
e) processing means for providing model parameters from data variables of the sample,
f) at least one storage means for storing physical parameters and/or data variables and/or model parameters of the biological sample,
g) at least one storage means for storing physical parameters and/or data variables and/or model parameters and characterisation information of a trained classification system,
h) means for correlating physical parameters and/or data variables and/or model parameters from the sample with physical parameters and/or data variables and/or model parameters of the trained system, and
i) means for displaying the characterisation class(es) of a sample.

In yet another aspect the invention relates to a method for characterising a biological sample of an animal, including a human, comprising
a) obtaining a biological sample from the animal or human,
b) exposing the sample to excitation light,
c) determining the physical parameter(s) of light emitted from the sample,
d) optionally performing a data handling of the obtained physical parameters obtaining data variables,
e) storing the physical parameters and/or data variables and/or model parameters,
f) optionally providing model parameters from data variables of the sample,
g) obtaining physical parameters and/or data variables and/or model parameters from a trained classification system,
h) correlating physical parameters and/or data variables and/or model parameters from the sample with physical parameters and/or data variables and/or model parameters of the trained system, and
i) displaying characterisation class(es) of the sample.

In yet another aspect the invention relates to a method for characterising a biological sample of an animal, including a human, comprising
a) obtaining a biological sample from the animal or human,
b) exposing the sample to excitation light,
c) determining the physical parameter(s) of light emitted from the sample, d) performing a data handling of the obtained physical parameters obtaining data variables,
e) storing the physical parameters and/or data variables and/or model parameters,
f) optionally providing model parameters from data variables of the sample,
g) obtaining physical parameters and/or data variables and/or model parameters from a trained classification system,
h) correlating physical parameters and/or data variables and/or model parameters from the sample with physical parameters and/or data variables and/or model parameters of the trained system, and
i) displaying characterisation class(es) of the sample.

In yet another aspect the invention relates to a method for characterising a biological sample of an animal, including a human, comprising
a) obtaining a biological sample from the animal or human,
b) exposing the sample to excitation light,
c) determining the physical parameter(s) of light emitted from the sample,
d) performing a data handling of the obtained physical parameters obtaining data variables,
e) storing the physical parameters and/or data variables and/or model parameters,
f) providing model parameters from data variables of the sample,
g) obtaining physical parameters and/or data variables and/or model parameters from a trained classification system,
h) correlating physical parameters and/or data variables and/or model parameters from the sample with physical parameters and/or data variables and/or model parameters of the trained system, and
i) displaying characterisation class(es) of the sample.

Thus, the comparison of the sample and the classification information in the trained classification system can be carried out on different levels of data, namely by comparing either the physical parameters and/or the data variables and/or the model parameters. It is likewise conceivable that two of the levels of data or all three levels can be used in the comparison of the biological sample to the classification information in the trained classification system.

According to the first aspect of the invention, namely the method of training a classification system, step b) which relates to obtaining classification information related to each biological sample can be carried out at any point in time as long as the information is available for the last step (step h) of the training method.

According to a preferred embodiment of the three aspects of the invention, the model parameters are latent variables being weighted averages of the data variables.

The method is preferably carried out in a classification system trained according to the present invention.

DRAWINGS

FIG. 1. Fluorescence landscape of typical urine sample. Intensity is given as a function of excitation and emission wavelength.

Figure 2:
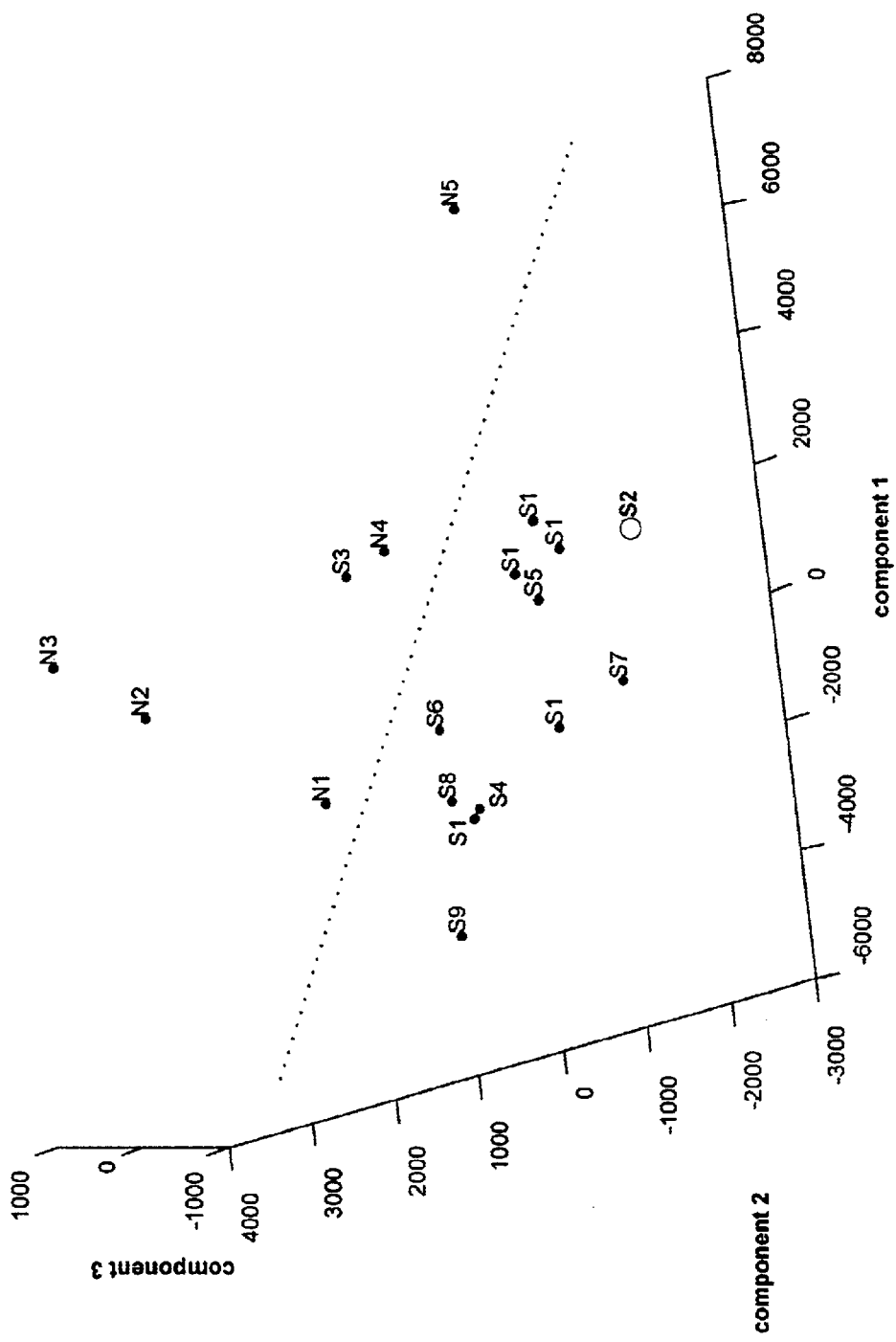

FIG. 2. Three-dimensional score plot of latent variable (component) one versus two versus three. The 18 samples are labelled according to smoker/non-smoker (S/N) and person (number).

Figure 3:
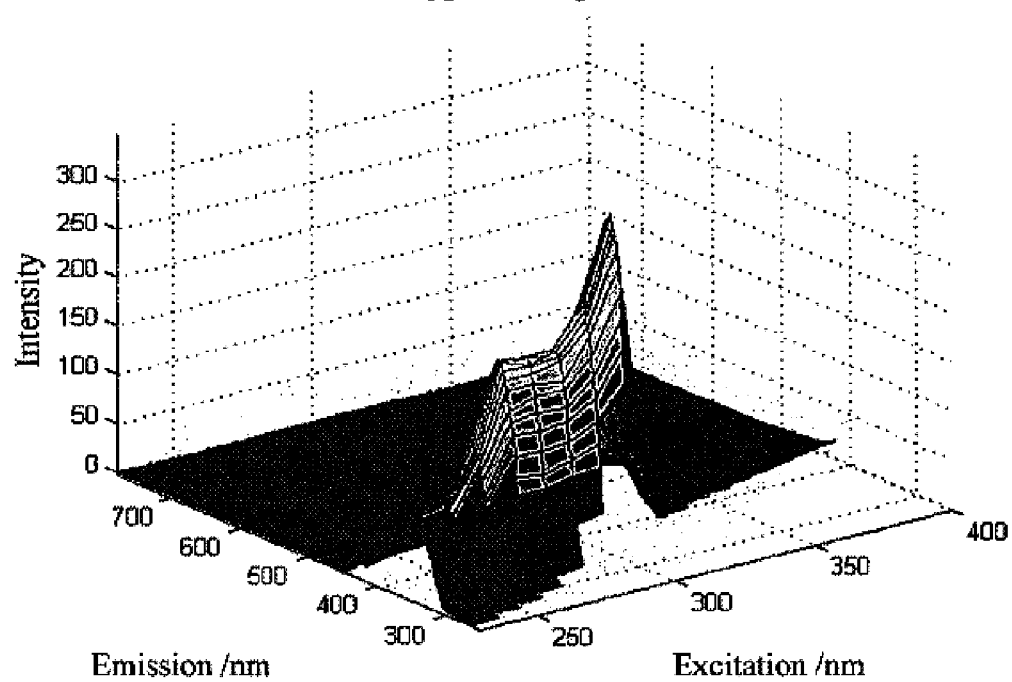

FIG. 3. Typical fluorescence excitation-emission landscape from a sample from a fasting person FIG. 4. A scatter plot of score one, two and five from a PCA model of 23 fasting and non-fasting persons.

Figure 5:
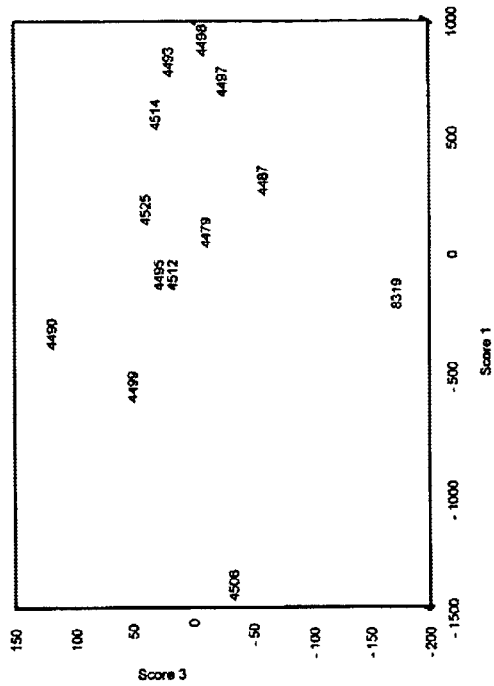
Figure 5:
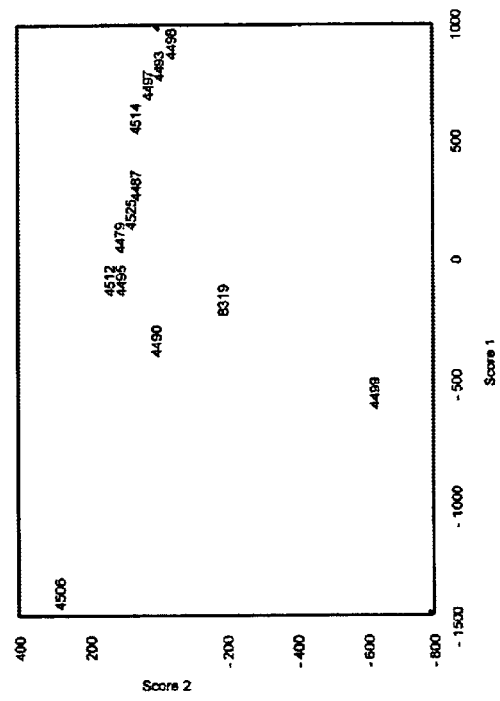
Figure 5:
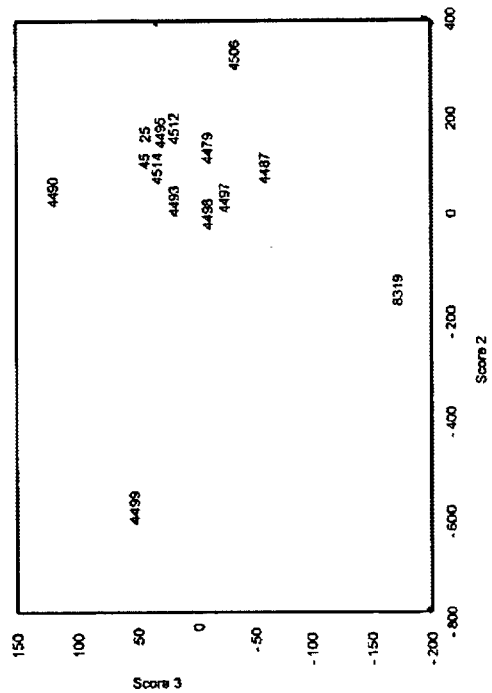

FIG. 5. Score scatter plots from a PCA model of data from persons with benign tumors. The plots show score 1 versus 2, 1 versus 3 and 2 versus 3.

Figure 6:
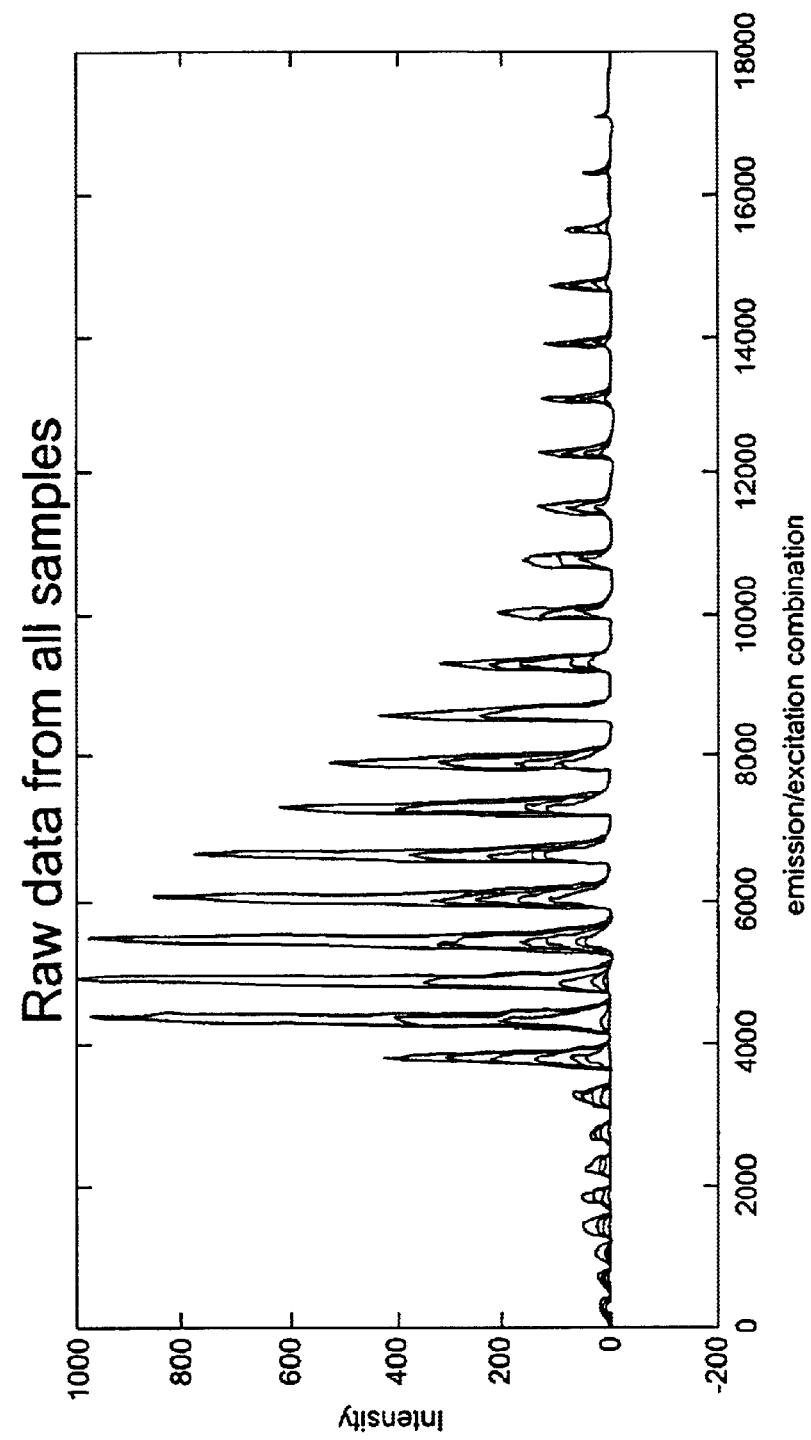

FIG. 6. A plot of the raw fluorescence data used in the analysis. The 28 spectra from each sample are arranged successively on an arbitrary wavelength scale.

Figure 7:
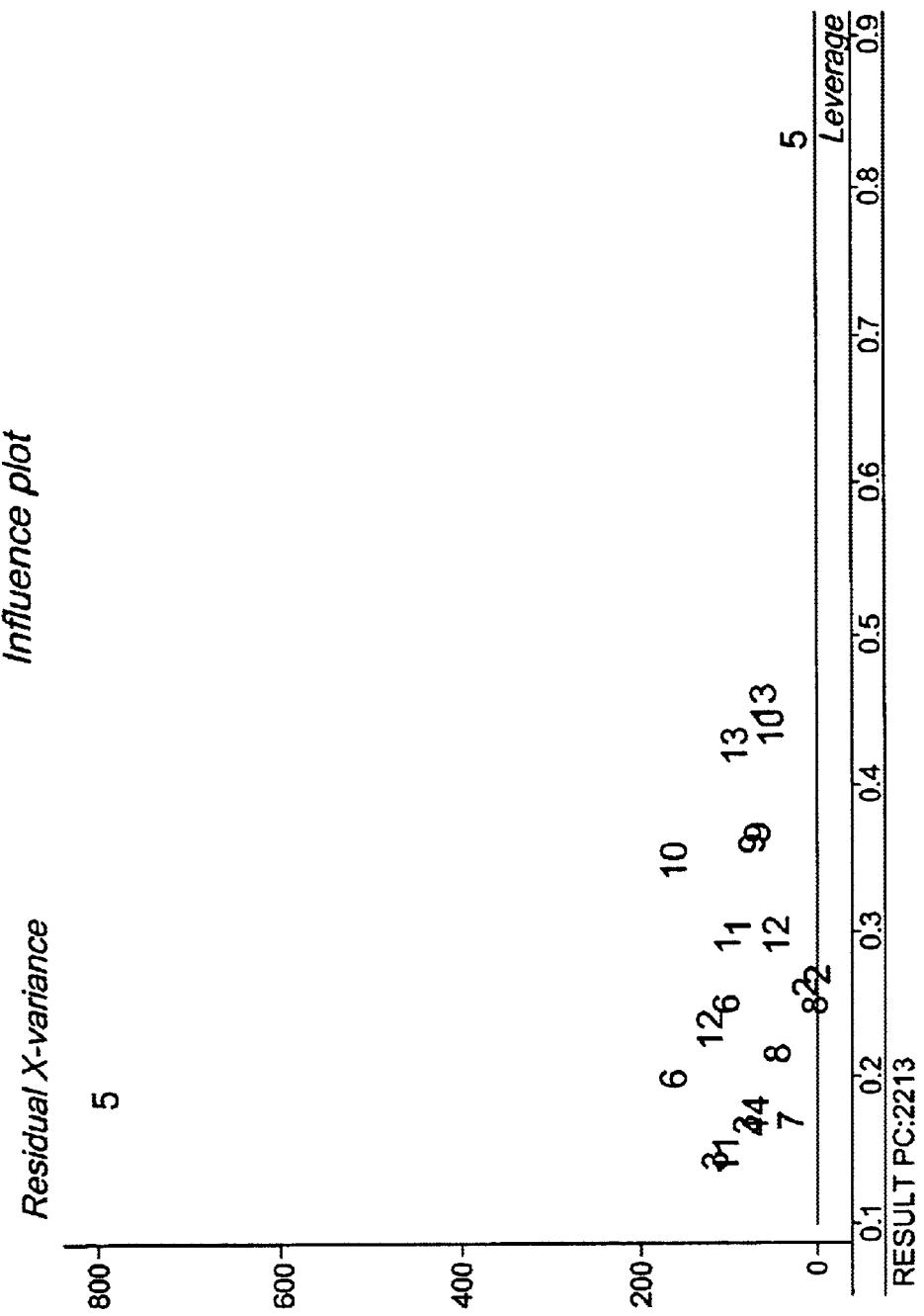

FIG. 7. Influence-plot of samples in two latent dimensions (bold) and in three latent dimensions (ordinary font). The behaviour of sample five going from poor description (high residual) to high impact on the model (high leverage) is indicative of an outlying behaviour. This sample is not visible as an outlier in the plot of the raw data (FIG. 6).

Figure 8:
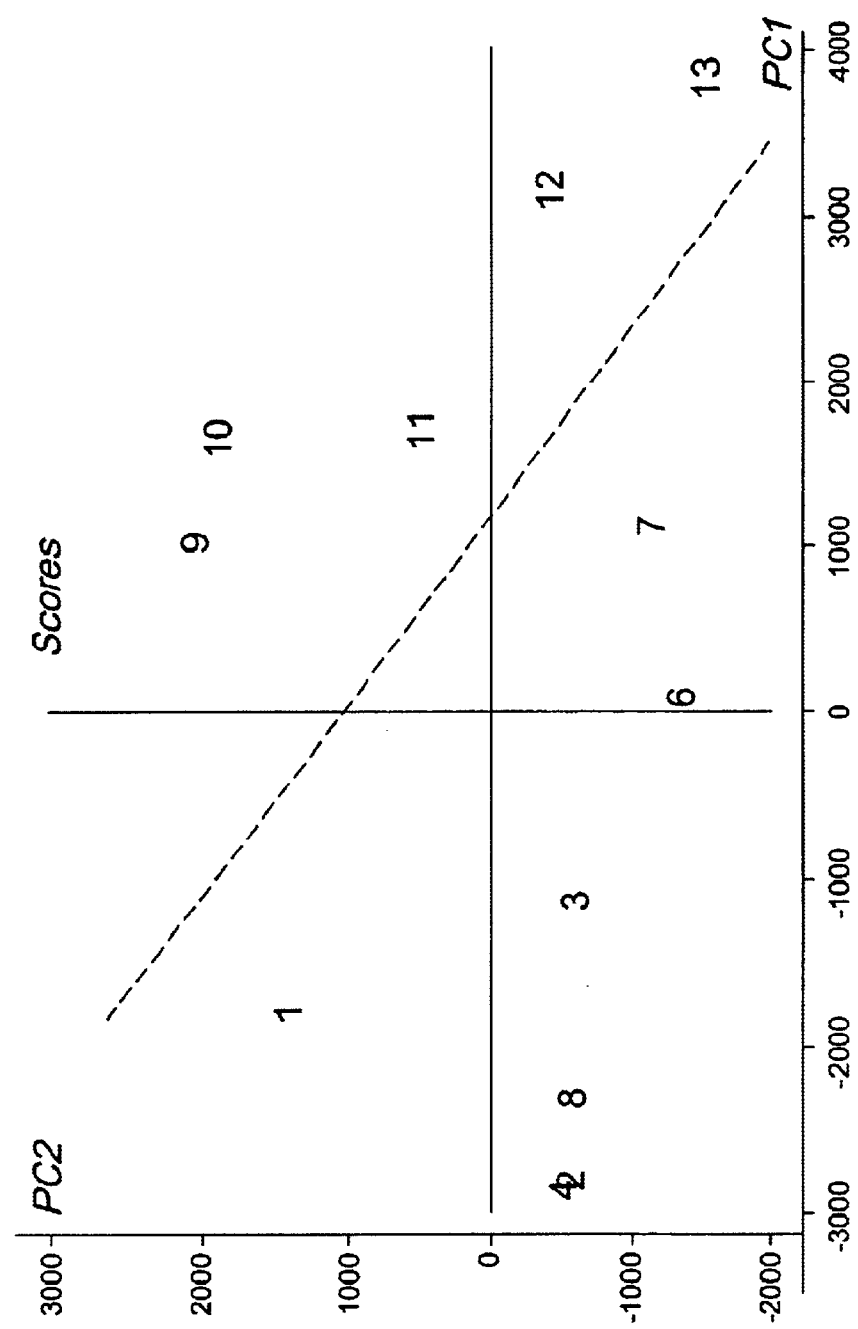

FIG. 8. Score-plot showing the samples from the cardiac patients investigation in terms of the first principal component versus the second principal component.

Figure 9:
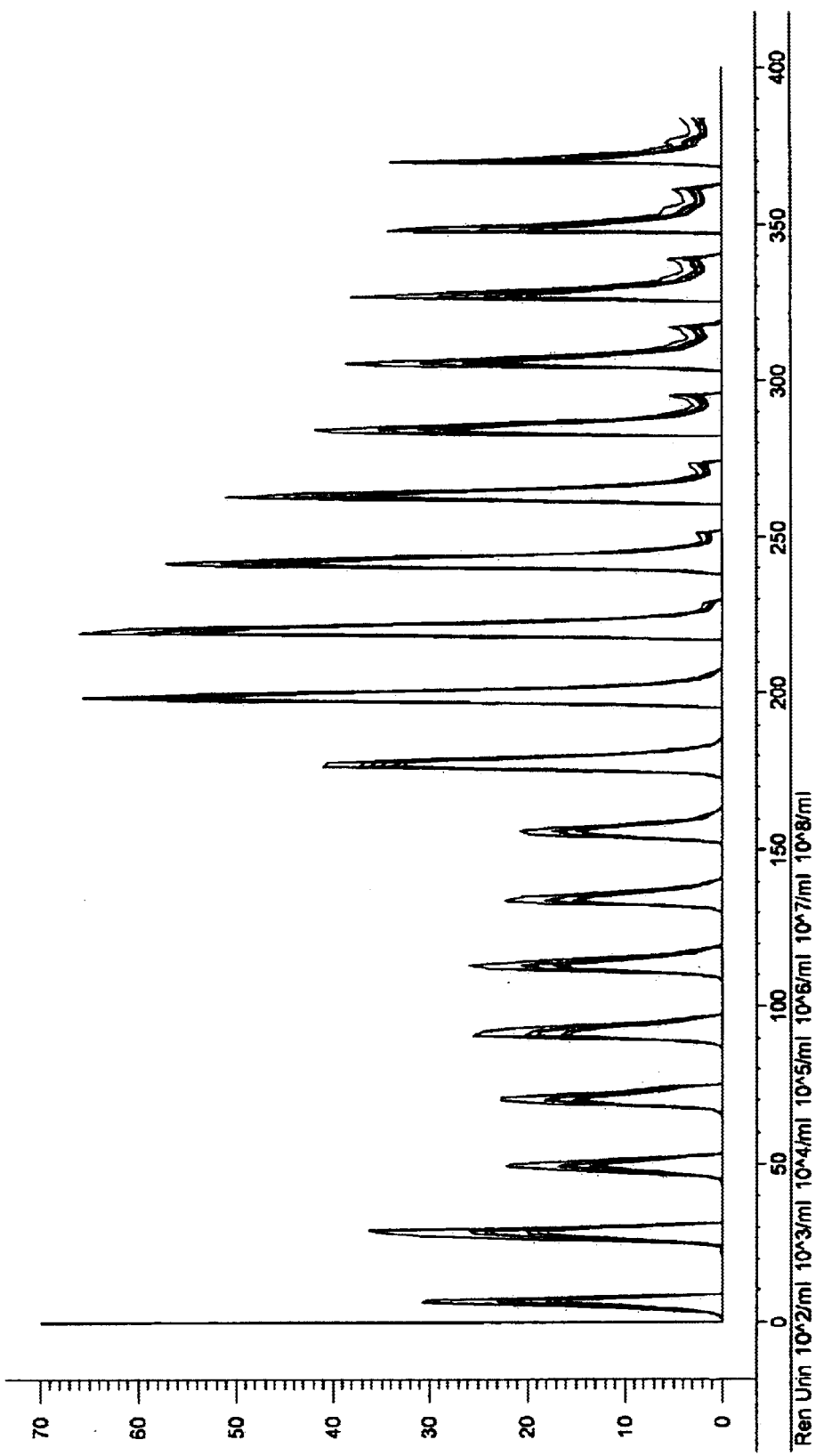

FIG. 9. Unfolded variable averaged fluorescence spectra for the 8 samples. The first emission top corresponds to excitation at 230 nm and the last emission top corresponds to excitation at 500 nm.

Figure 10B:
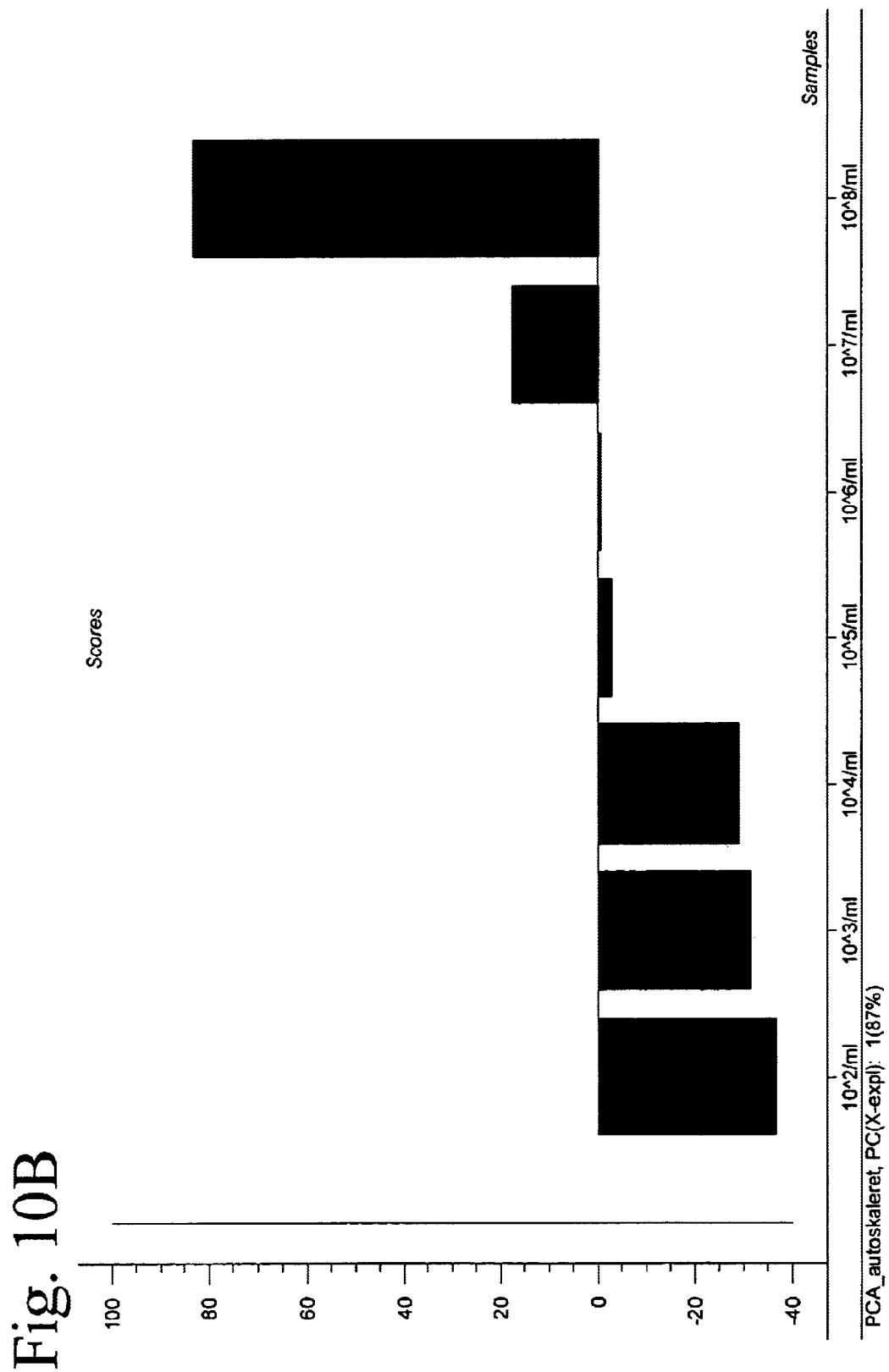

FIG. 10A. PC1 vs. PC2 score plot from a PCA on auto scaled data. FIG. 10B. PC1 score from a PCA on auto scaled data.

Figure 11A:
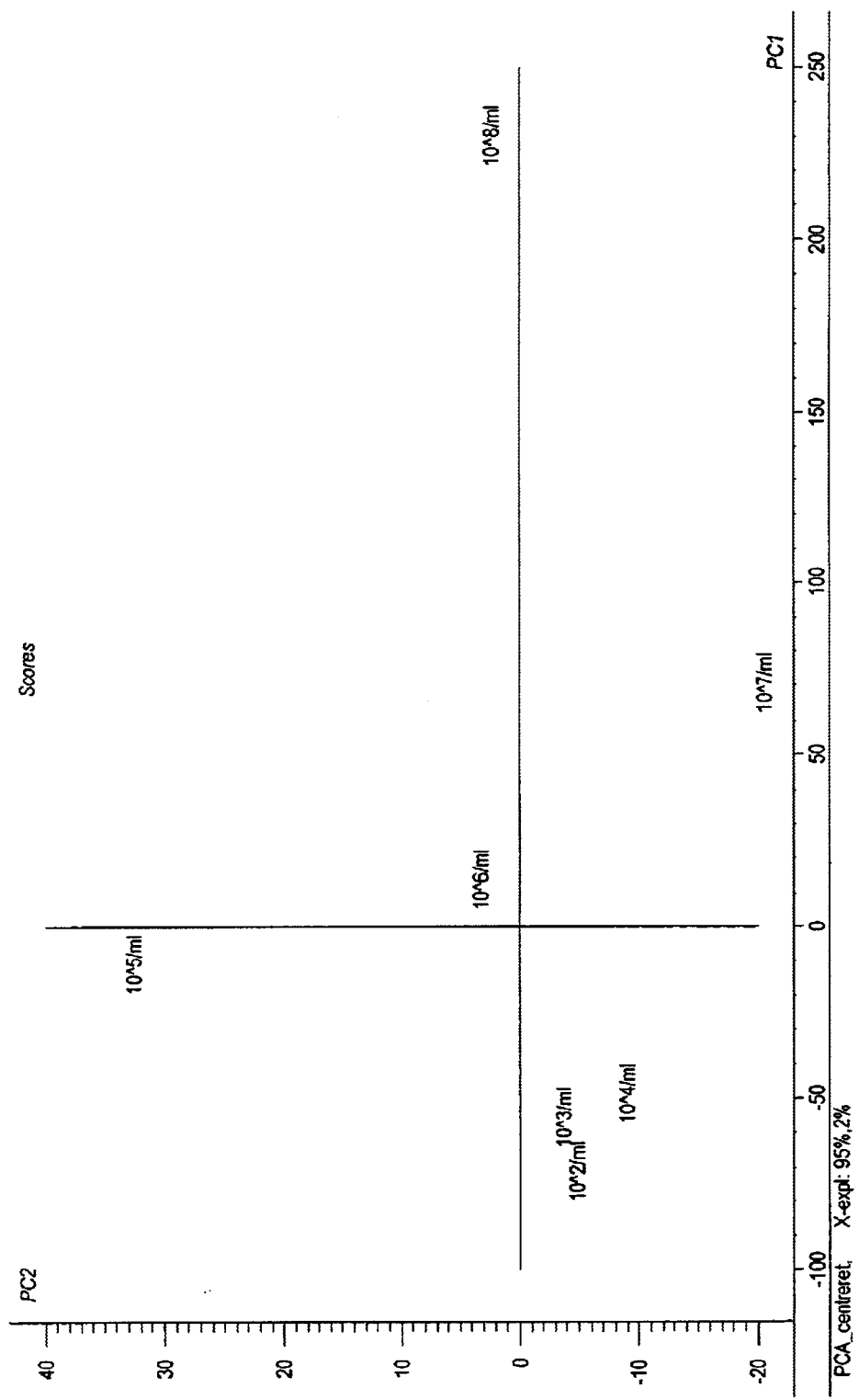
Figure 11B:
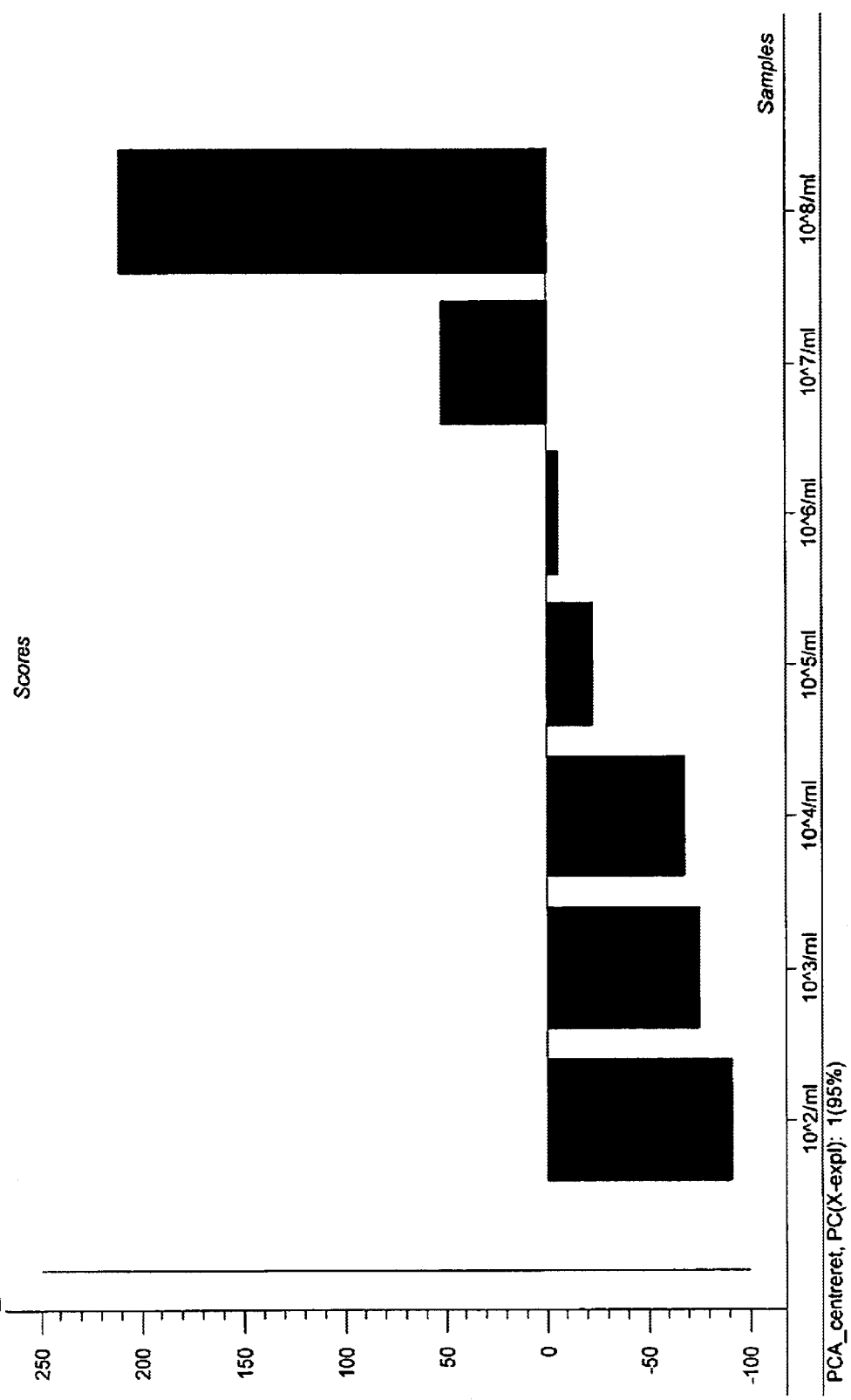

FIG. 11A PC1 vs. PC2 score plot from a PCA on mean centered data. FIG. 11B PC1 score from a PCA on mean centered data.

Figure 12B:
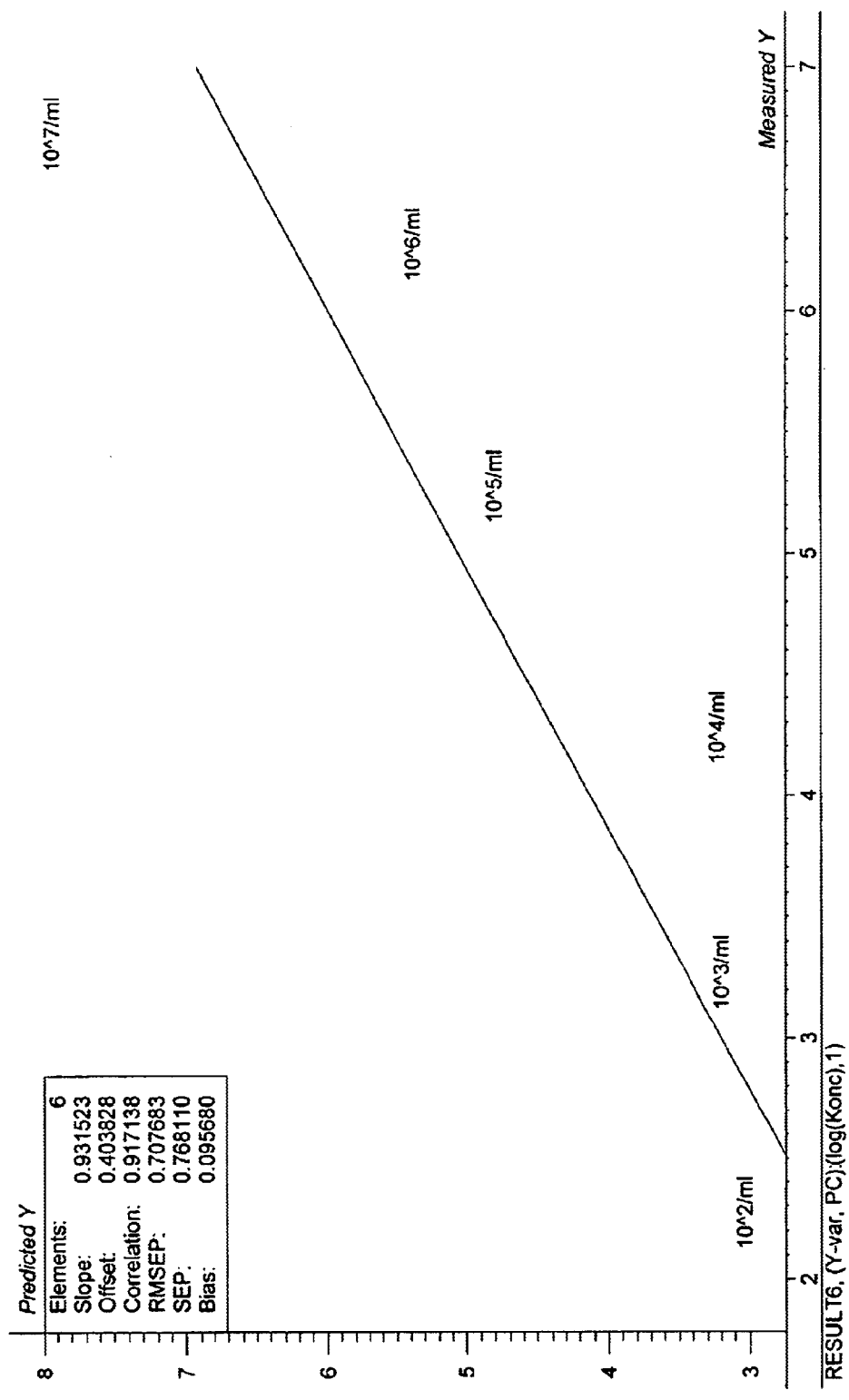

FIG. 12A Predicted vs. measured for log(concentration) with all bacteria samples (i.e. without control sample). FIG. 12B Predicted vs. measured for log(concentration) without the control sample and the sample containing $10^8$ cells.

Figure 13:
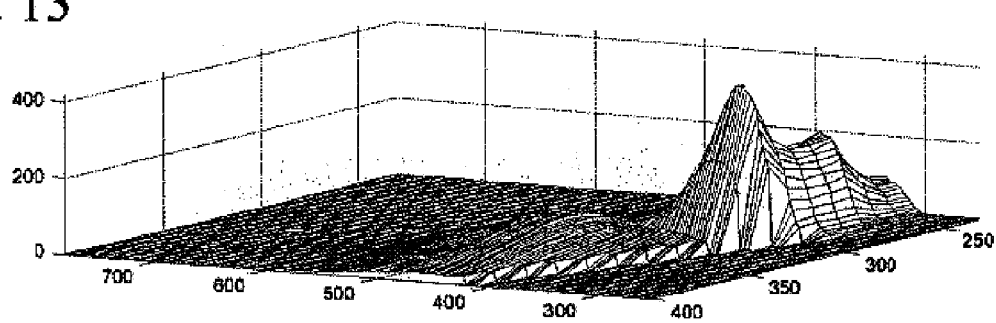
Figure 13:
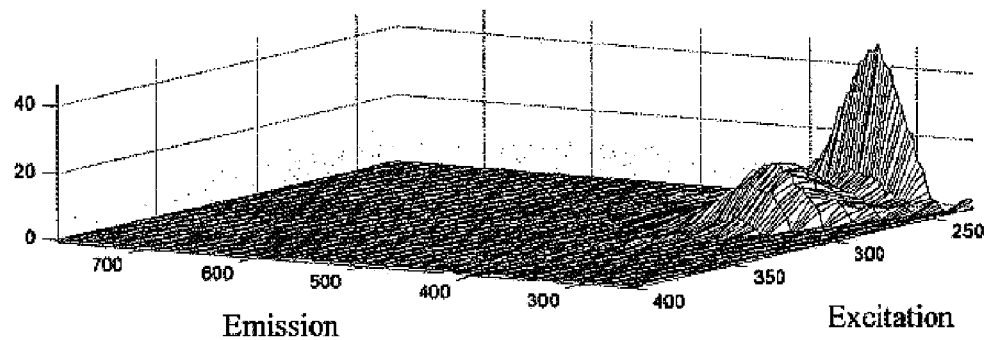

FIG. 13. Upper part: Front face fluorescence spectrum of an undiluted blood plasma sample. Lower part: Front face fluorescence spectrum of the same sample diluted 1:5000. Notice the different intensity scales.

Figure 14A:
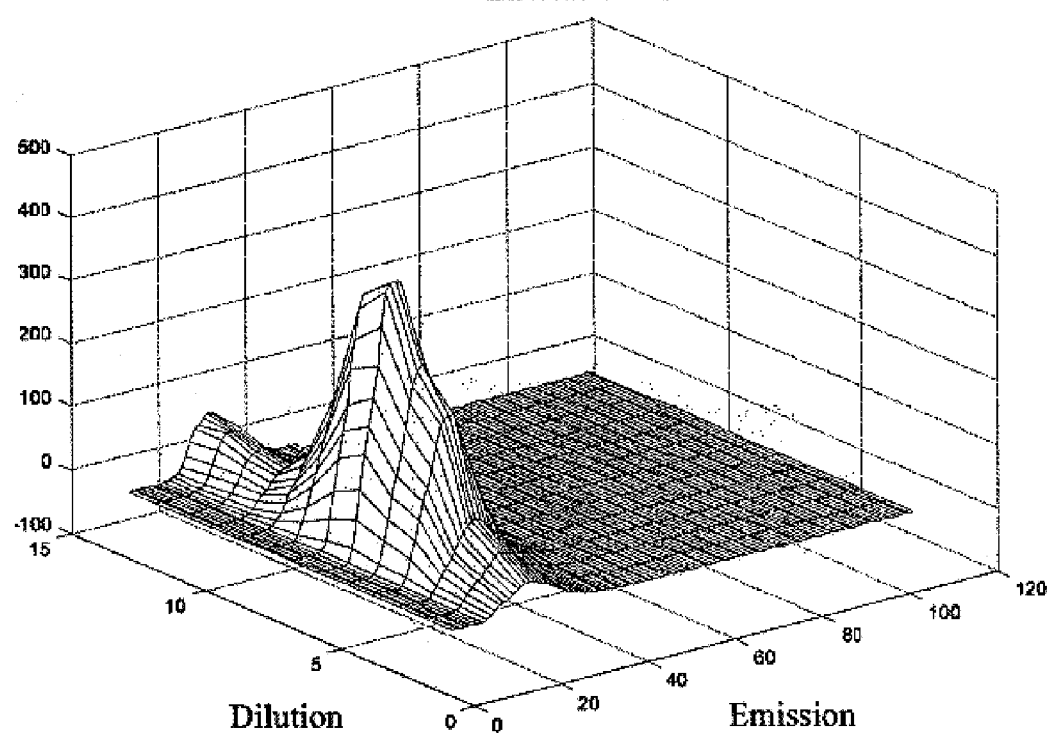
Figure 14B:
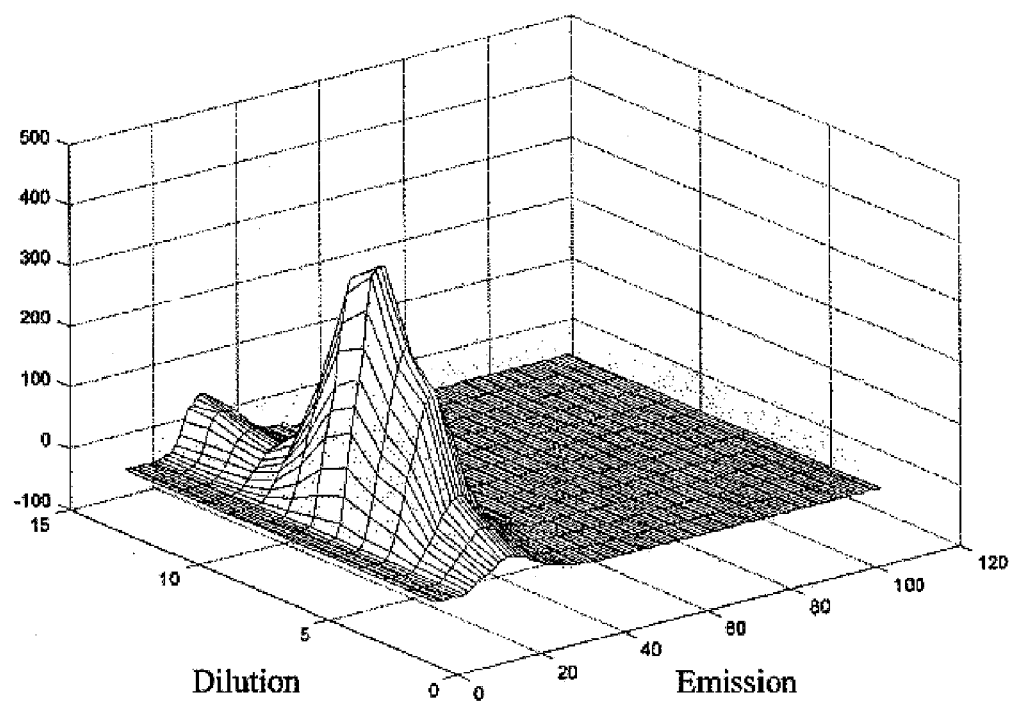

FIG. 14A. Excitation 230 nm as a function of the dilution. 2 is diluted 1:5000, 3 is 1:3000, 4 is 1:2000, 5 is 1:700, 6 is 1:500, 7 is 1:200, 8 is 1:100, 9 is 1:50, 10 is 1:25, 11 is 1:10, 12 is 1:5, 13 is 1:2, 14 is undiluted sample. FIG. 14B Excitation 250 nm as a function of the dilution. Same dilutions as in FIG. 14A. (Measured in front face mode).

Figure 15A:
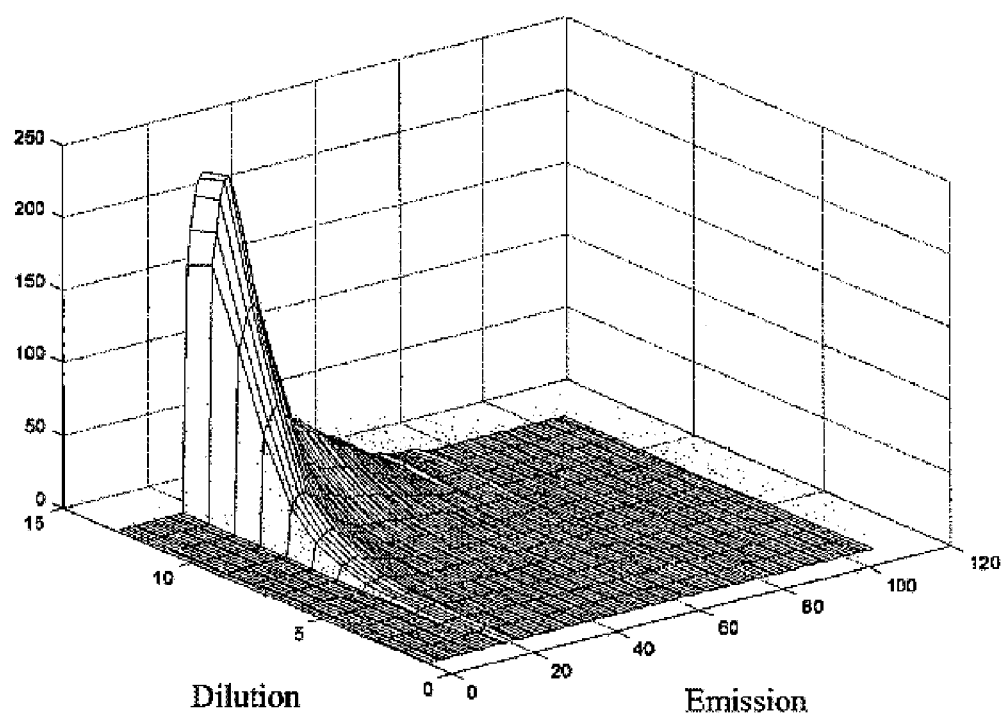

FIG. 15A Excitation 310 nm as a function of the dilution. Same dilutions as in FIG. 14A. Excitation 360 nm as a function of the dilution. Same dilutions as in FIG. 14A. (Measured in front face mode).

Figure 16A:
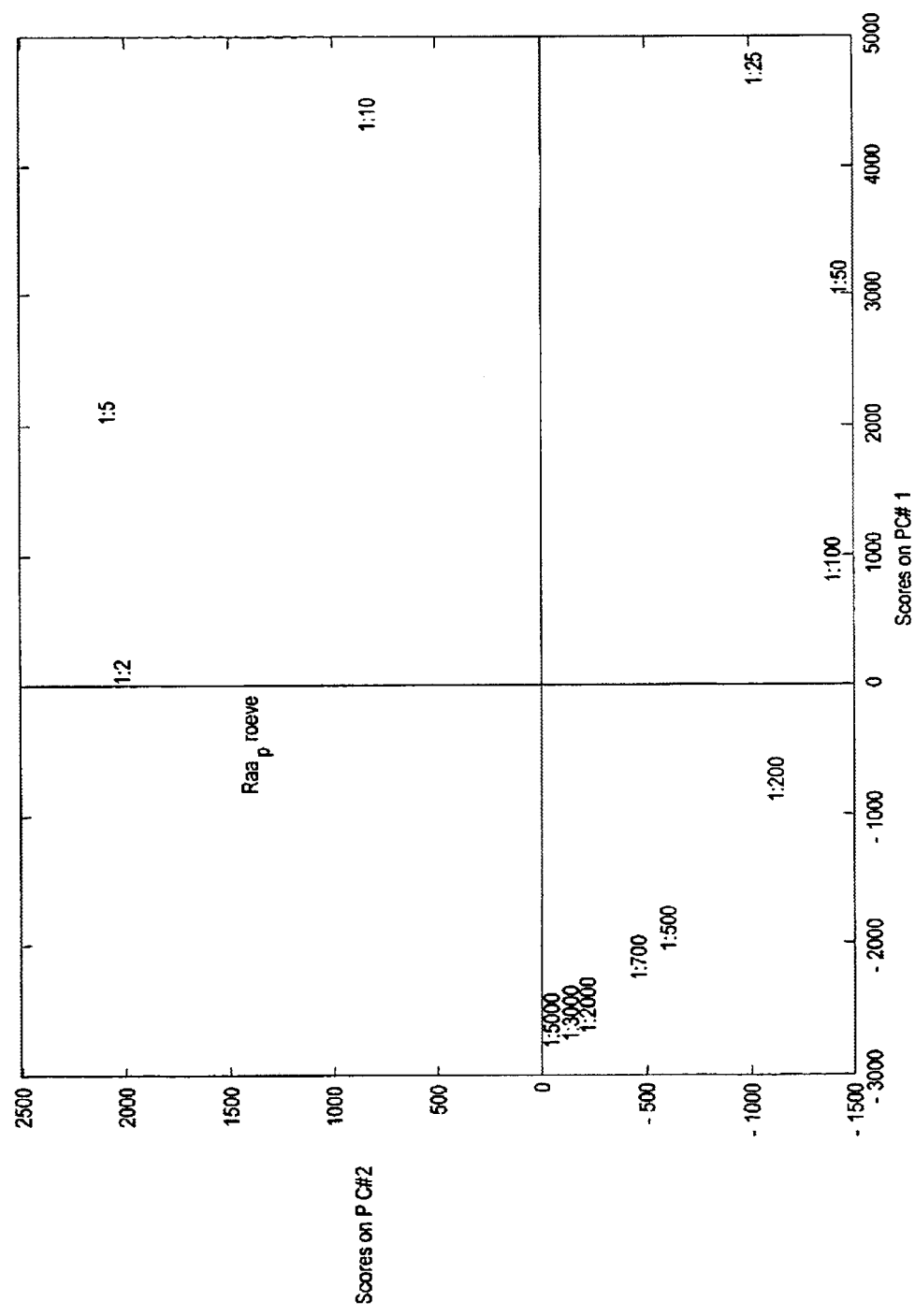
Figure 16B:
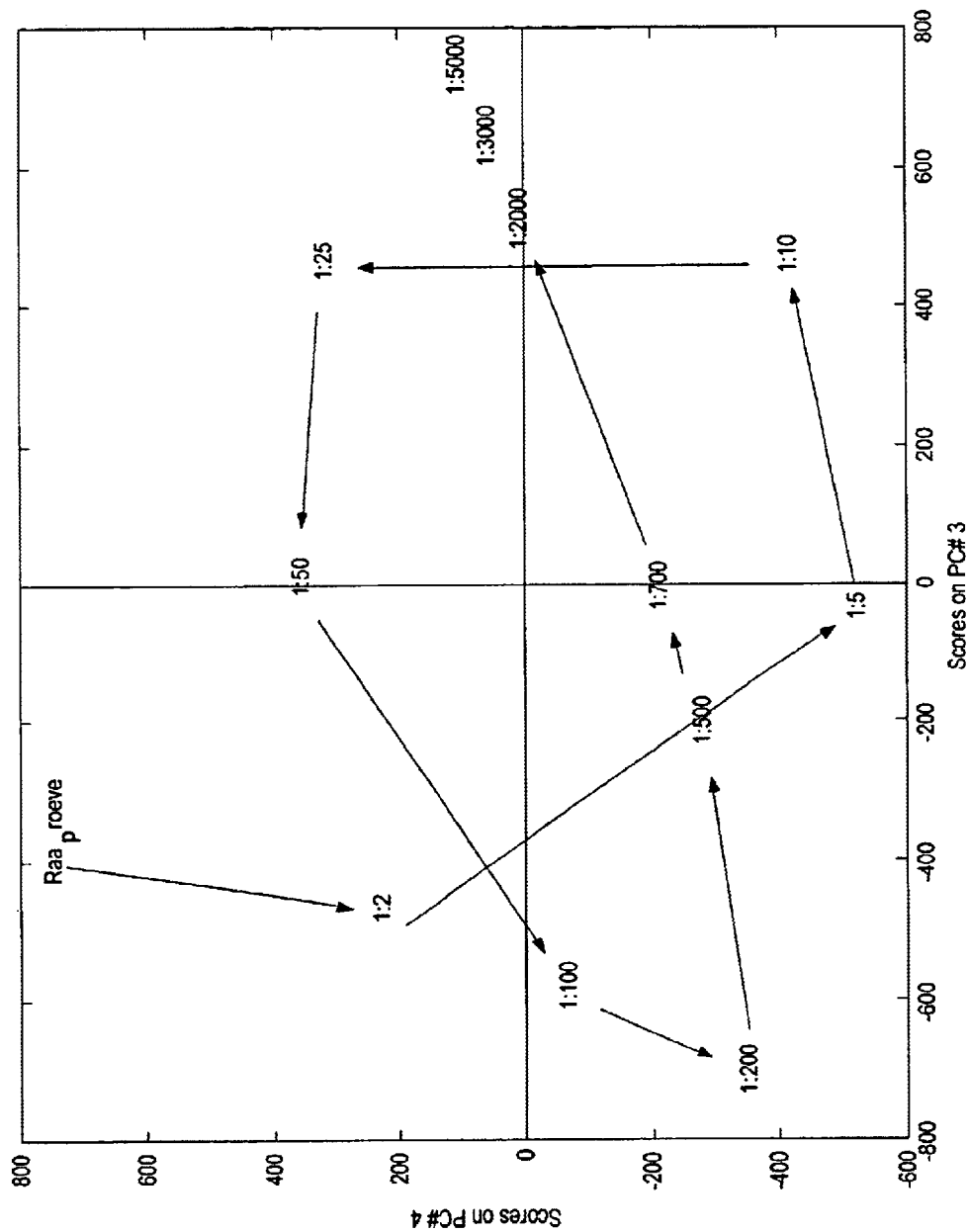

FIG. 16A. PC1 vs. PC2 score plot from a PCA. FIG. 16B. PC3 vs. PC4 score plot from a PCA FIG. 17. Upper part: Transmission fluorescence spectrum of an undiluted blood plasma sample. Lower part: Transmission fluorescence spectrum of the same sample diluted 1:5000. Notice the different intensity scales.

Figure 18A:
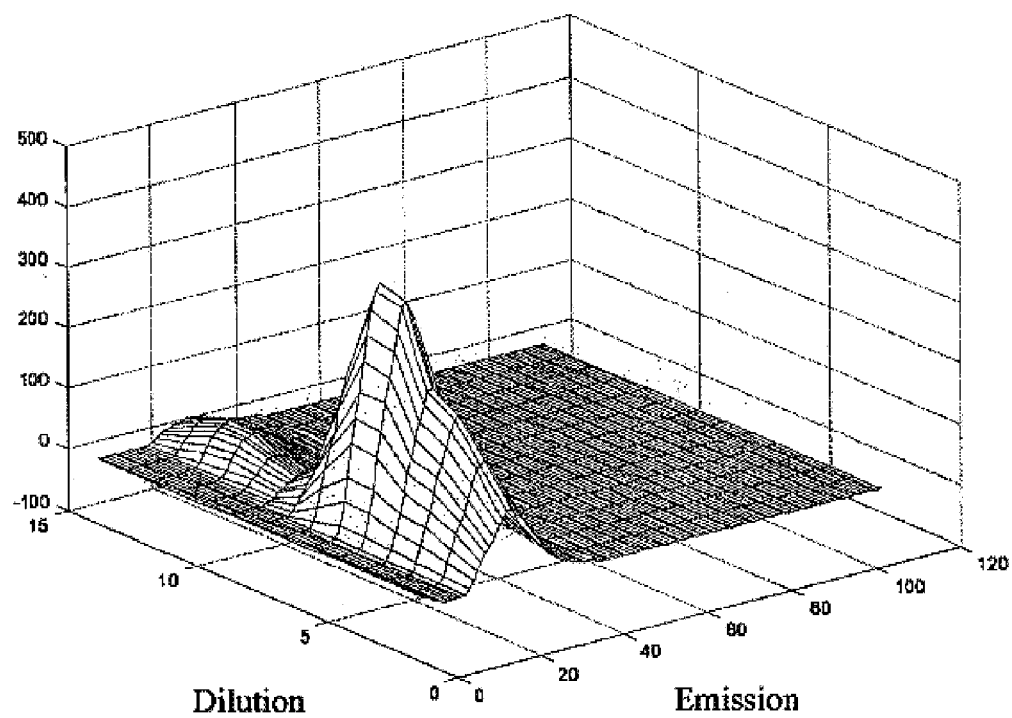
Figure 18B:
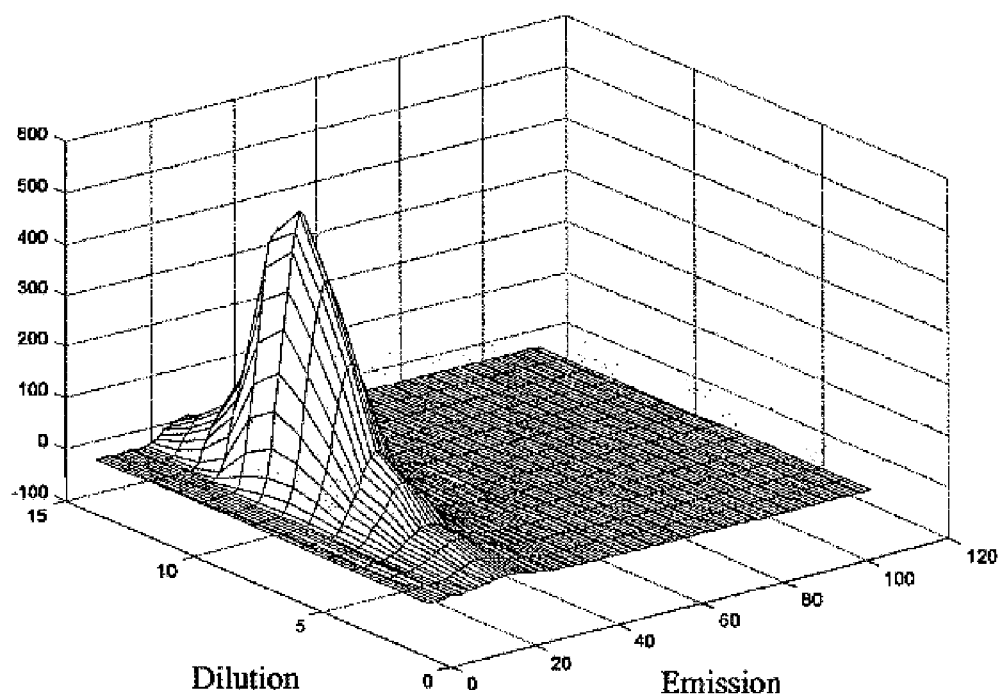

FIG. 18A. Excitation 230 nm as a function of the dilution. 2 is diluted 1:5000, 3 is 1:3000, 4 is 1:2000, 5 is 1:1000, 6 is 1:700, 7 is 1:500, 8 is 1:200, 9 is 1:100, 10 is 1:50, 11 is 1:25, 12 is 1:10, 13 is 1:5, 14 is 1:2, 15 is undiluted sample. FIG. 18B. Excitation 250 nm as a function of the dilution. Same dilutions as in FIG. 18A. (Measured in transmission mode).

Figure 19A:
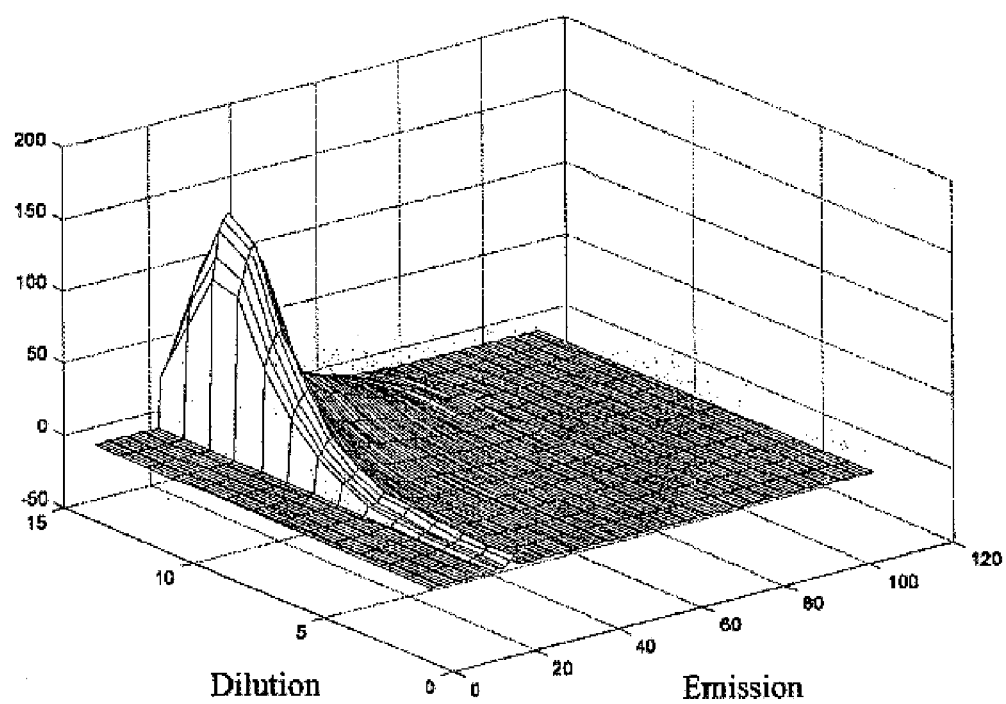

FIG. 19A. Excitation 310 nm as a function of the dilution. Same dilutions as in FIG. 18A. FIG. 19B. Excitation 360 nm as a function of the dilution. Same dilutions as in FIG. 18A. (Measured in transmission mode).

Figure 20A:
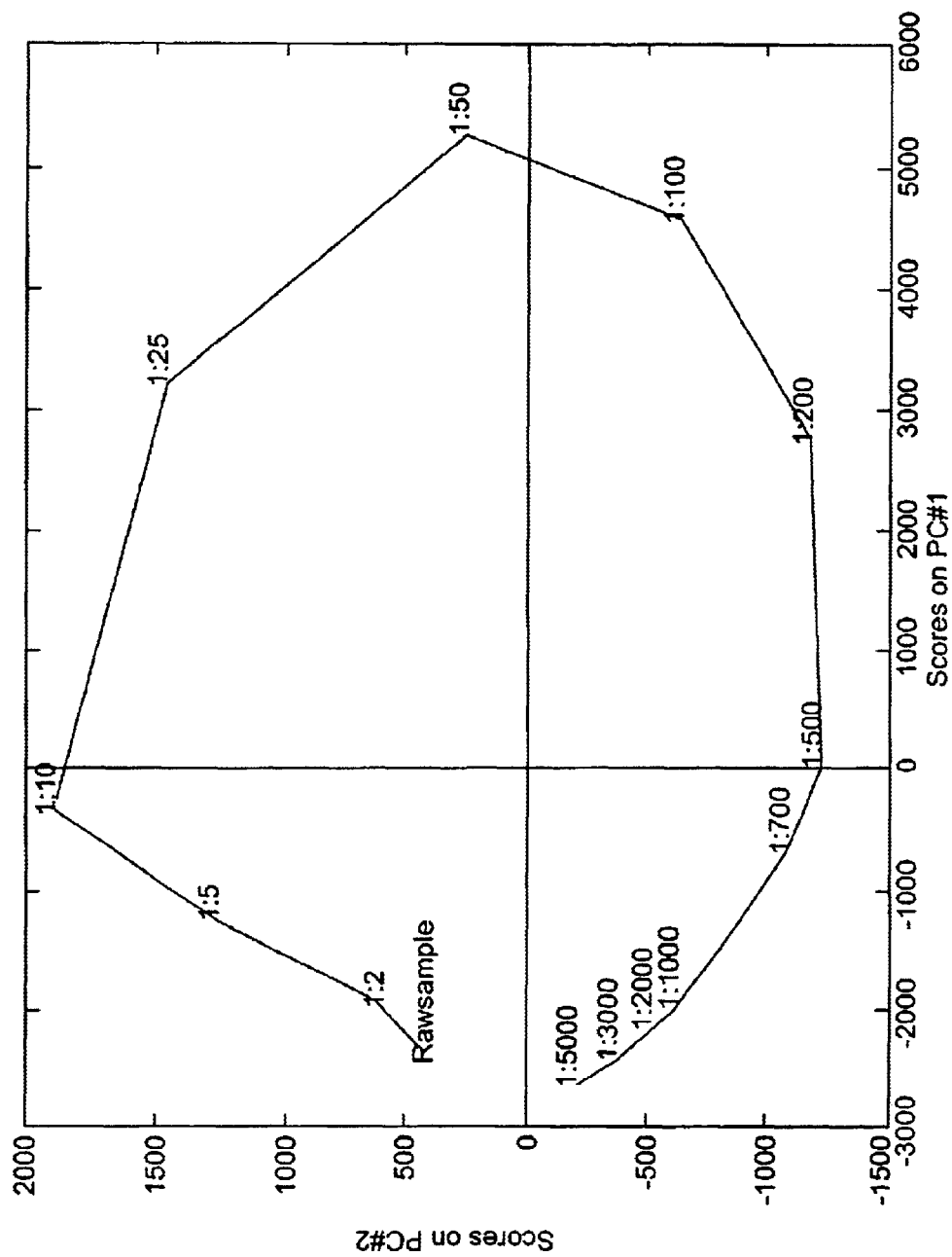
Figure 20B:
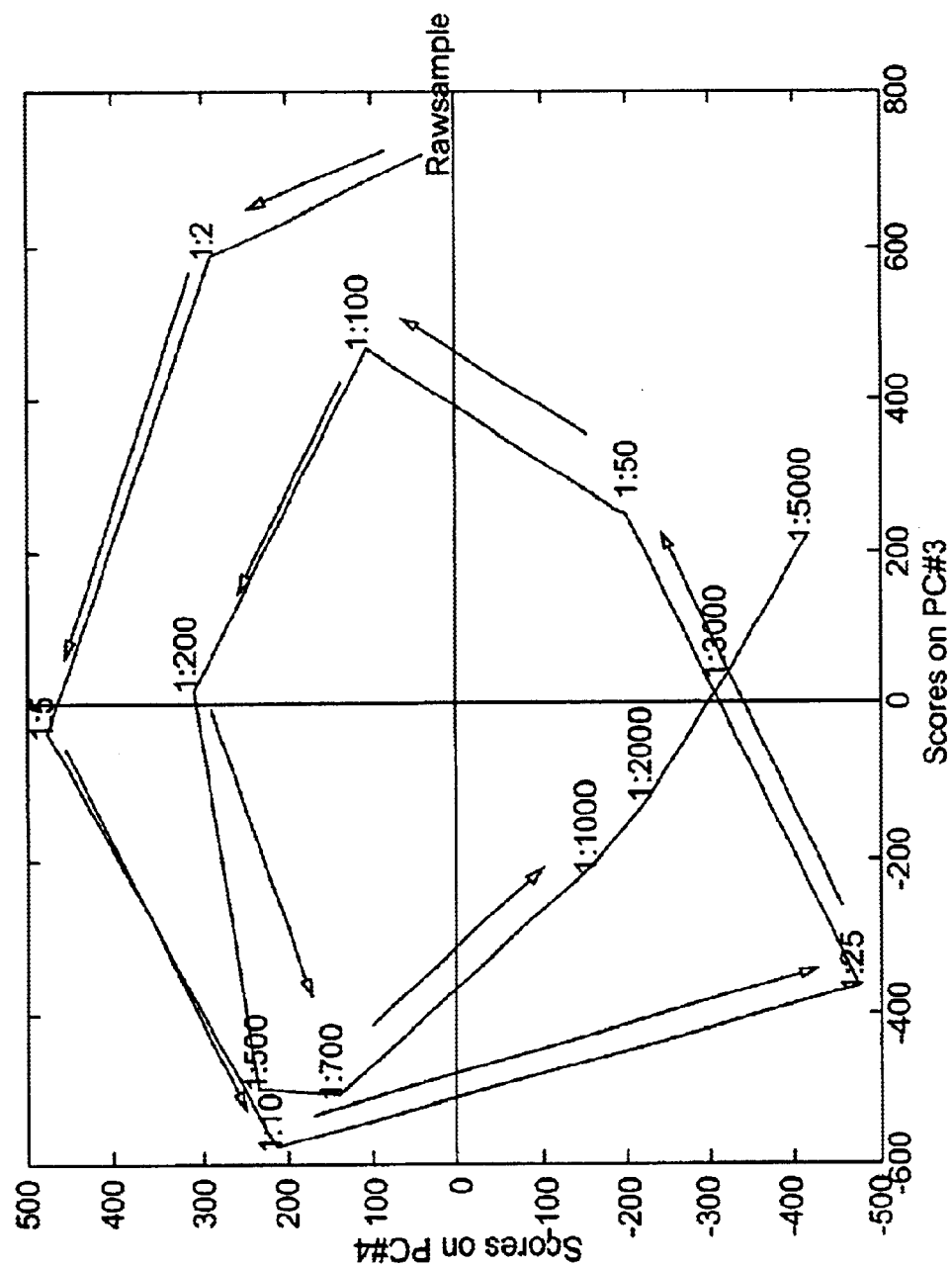

FIG. 20A. PC1 vs. PC2 score plot from a PCA. FIG. 20B. PC3 vs. PC4 score plot from a PCA.

Figure 21A:
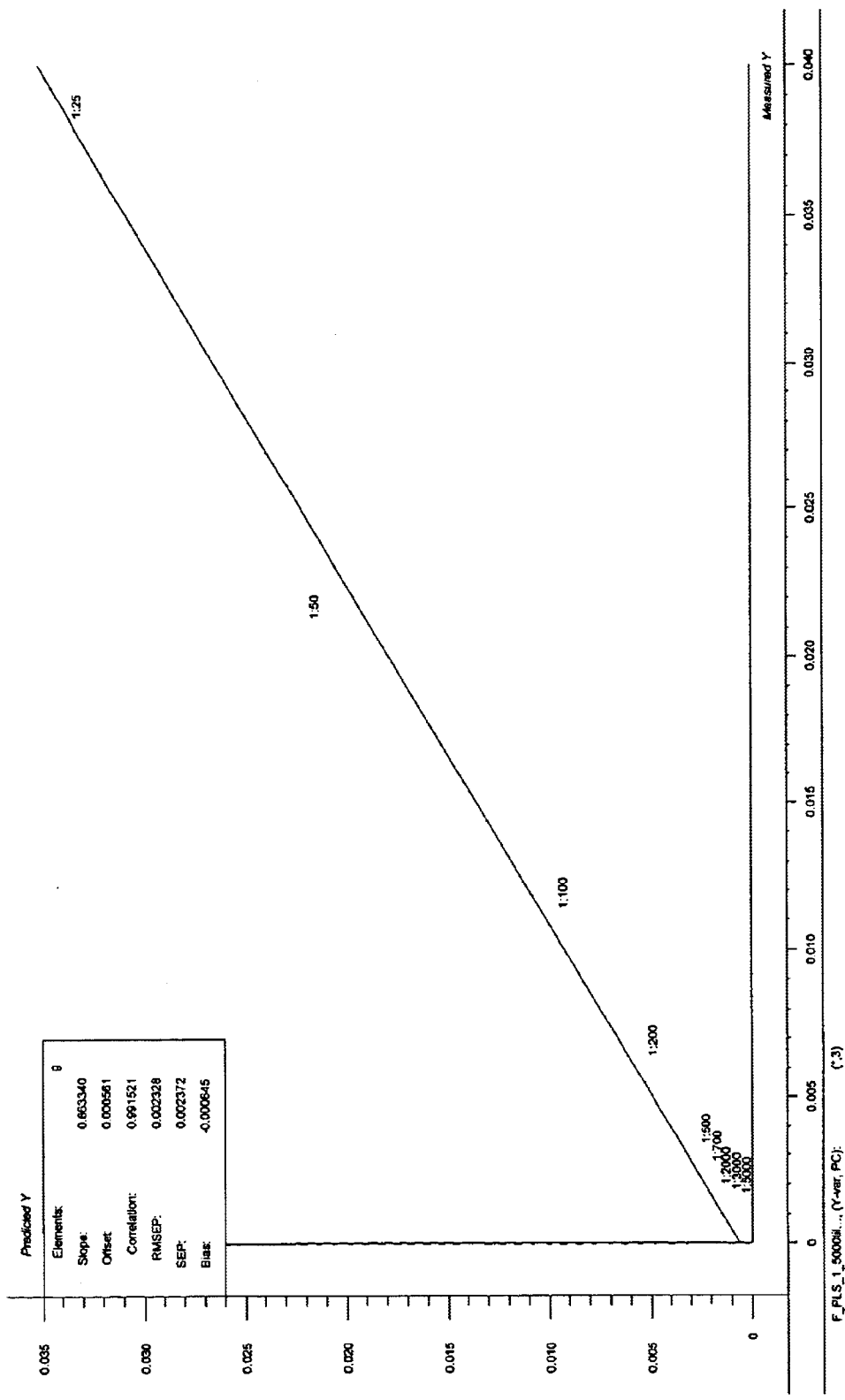
Figure 21B:
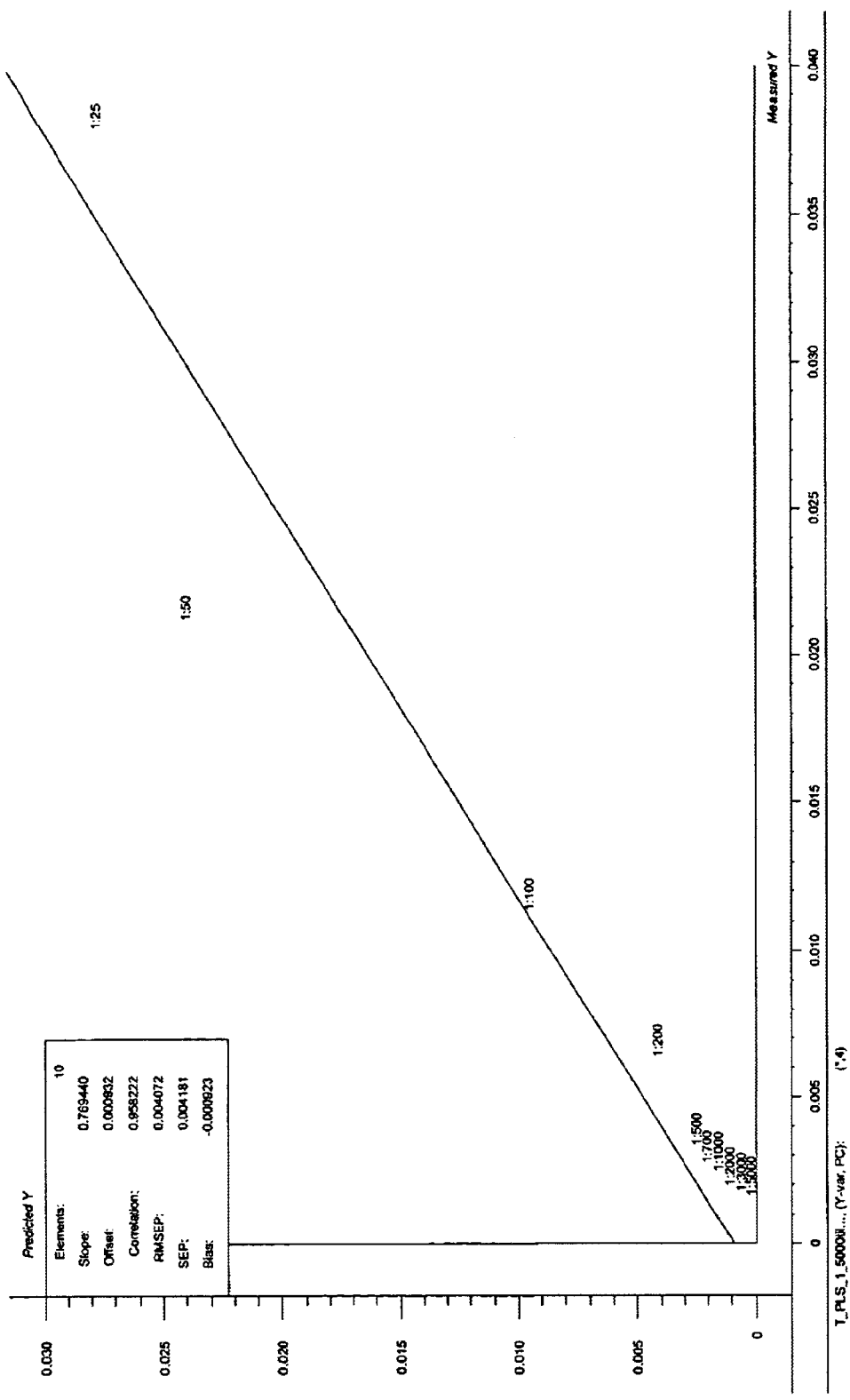

FIG. 21A. Predicted vs. measured for front face for 1:25 to 1:5000. FIG. 21B Predicted vs. measured for transmission for 1:25 to 1:5000.

Figure 22A:
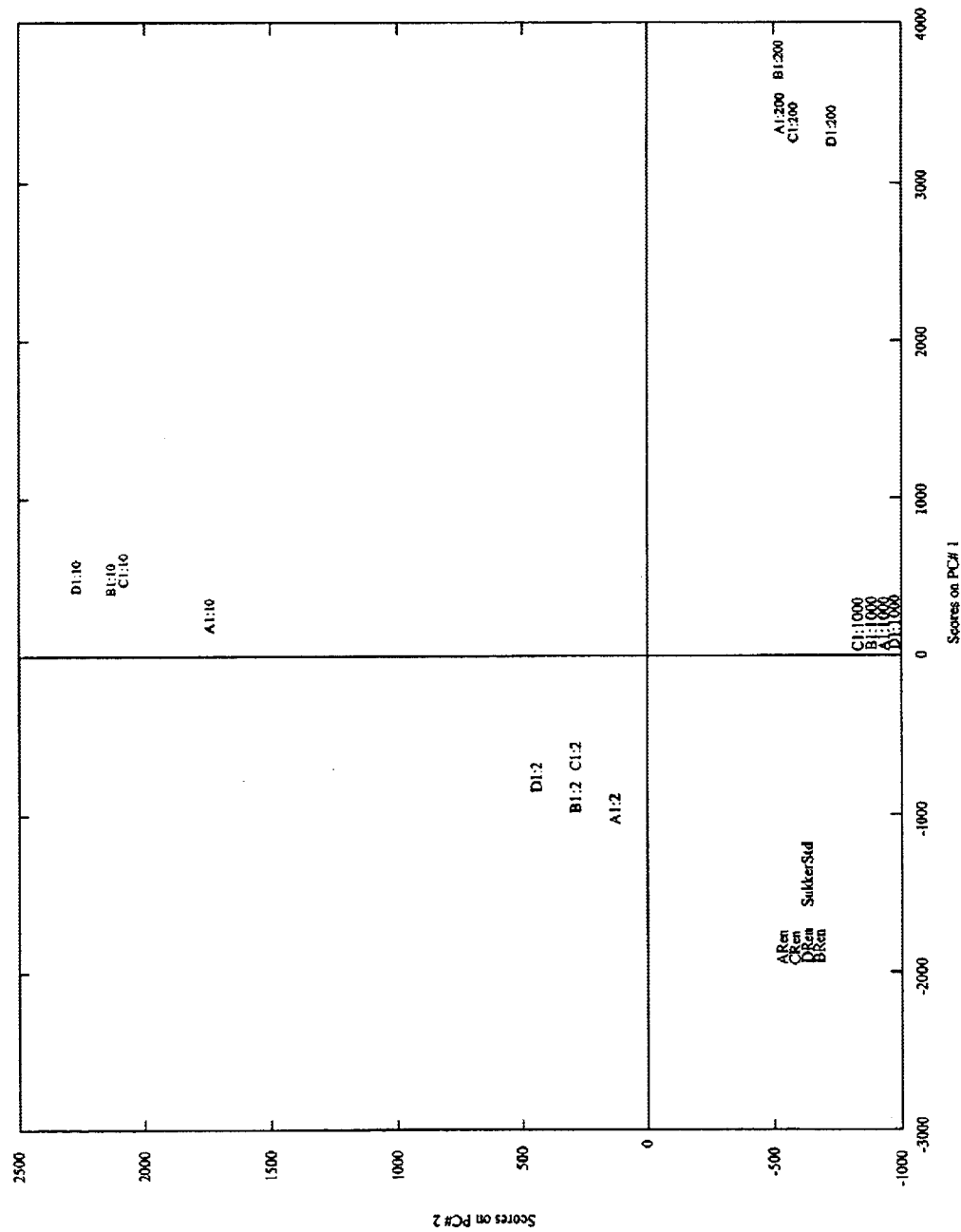
Figure 22B:
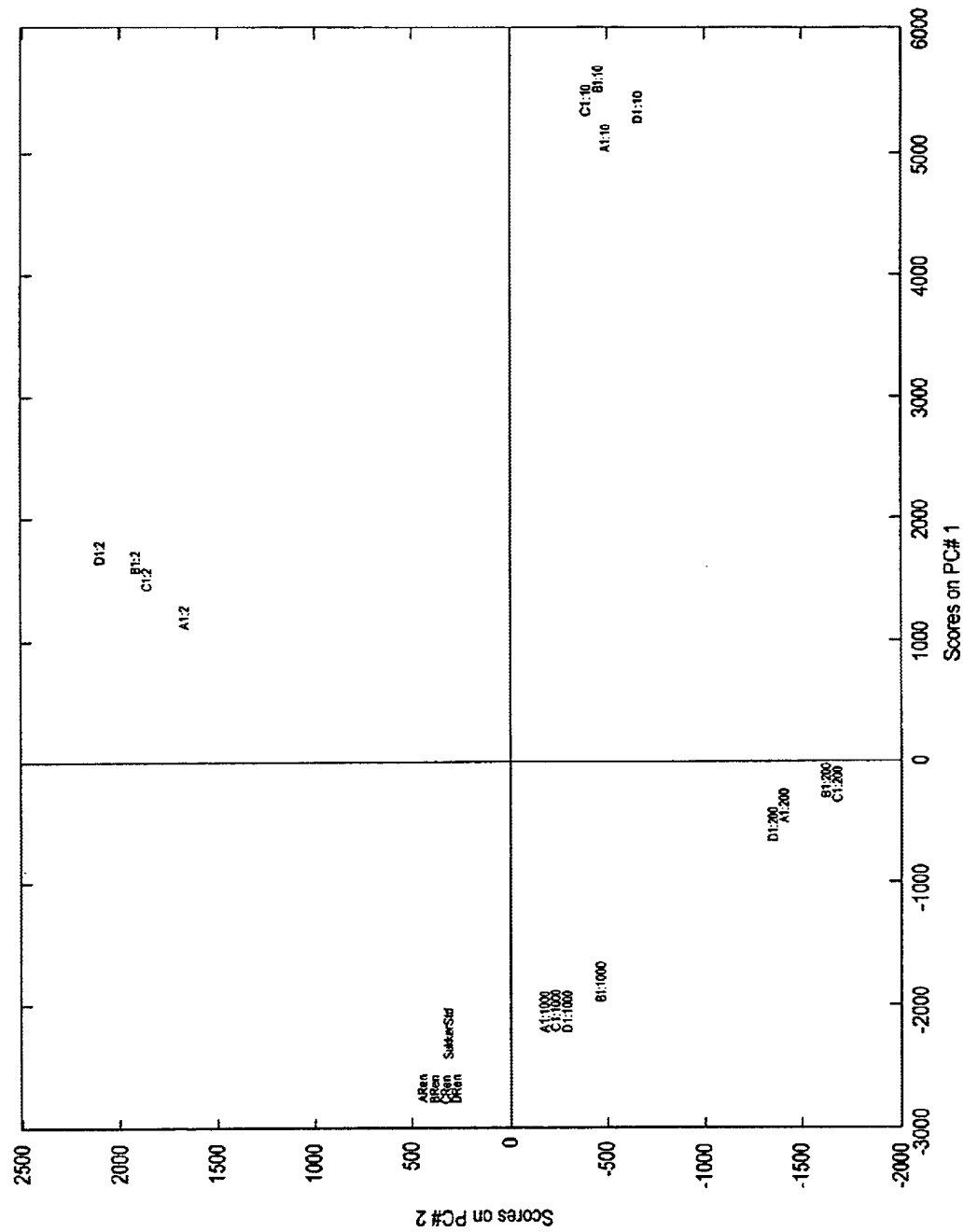

FIG. 22A. PC1 vs. PC2 score plot from a PCA on transmission samples. A, B, C, and D are different buffers with pH values of approx. 8.5–9.0, 7.0–7.5, 5.0–6.5, and 0.1 M HCl, respectively. Numbers like 1:2 indicate the dilution factor. FIG. 22B PC1 vs. PC2 score plot from a PCA on front face samples.

Figure 23:
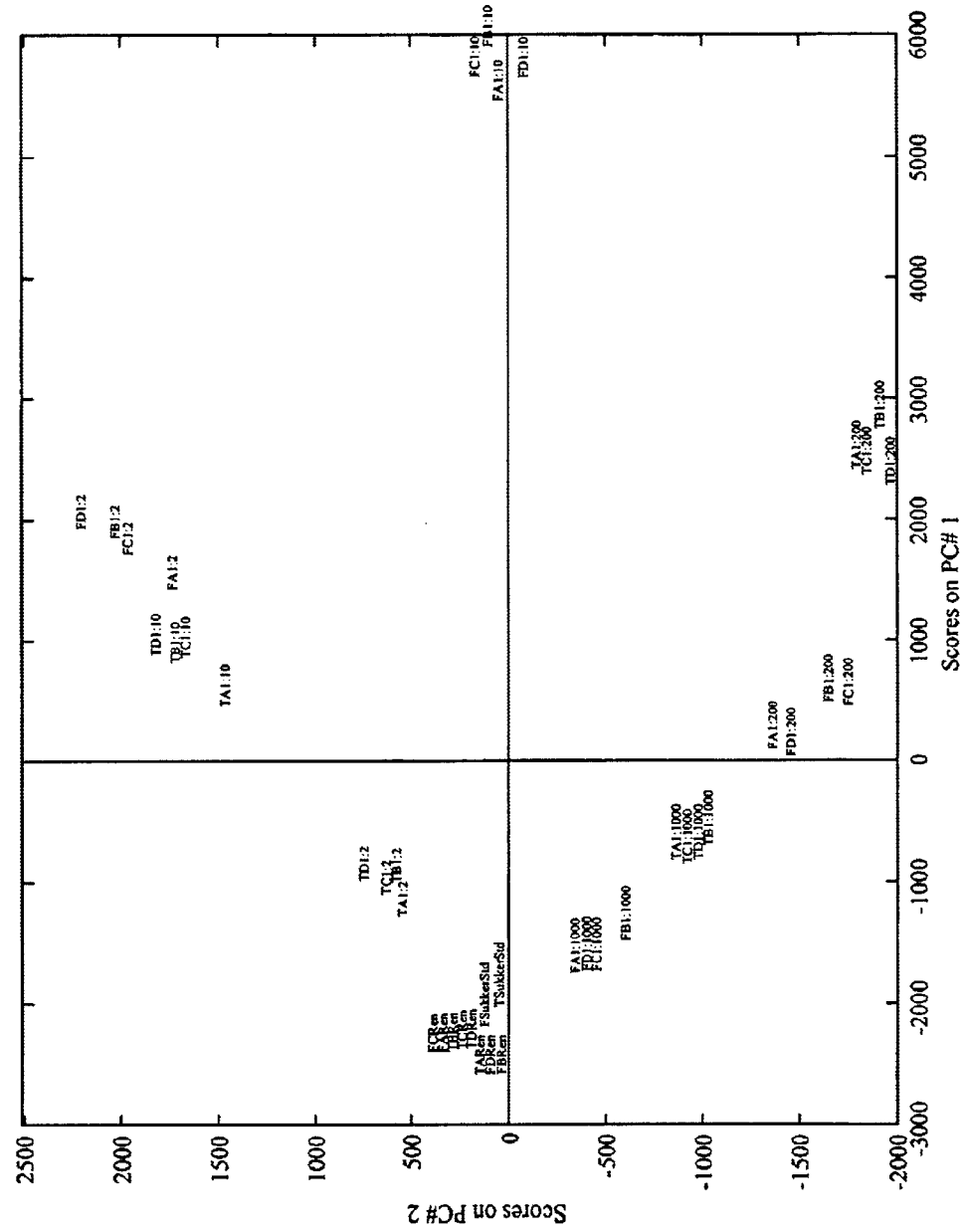

FIG. 23 PC1 vs. PC2 from a PCA on all samples. F is front face and T is transmission FIG. 24. Unfolded fluorescence spectra at four different pH values for transmission mode samples diluted 1:10. The difference observed for 0.1 M HCl spectrum seen in insert B is not observed for the other dilutions.

DETAILED DESCRIPTION OF THE INVENTION

The invention relates to classification based on physical parameters obtained from the luminescence spectroscopy oh light emitted from the sample. For practical reasons most of the discussion in this description relates to fluorescence spectroscopy. However as described below other physical parameters may be used in the classification. Thus, throughout the description the term fluorescence is used as an equivalent of any luminescence type and is to be interpreted as such, unless disappropriate in specific embodiments.

Fluorescence spectroscopy is an extremely sensitive tool. The data obtained from a spectrofluorimetric analysis can be considered a finger-print of the sample. Each sample gives rise to a unique spectrofluorometric set of physical parameters, however, as is described by the present invention. When analysing the fluorescence data, it has become possible to classify samples into two or more classes based on the fluorescence spectra, if there is any systematic difference between the samples. The difference between the samples will mostly not relate to a single component or a few components of the sample, but rather to a combination of a wide variety of components. This combination exhibits a pattern so complex that it is detectable by multivariate analysis only.

Thus, according to the evaluation of the fluorescence parameters it is possible to obtain more information about a biological sample, than it is when evaluating the various chemical components in the sample individually, i.e. it is possible to obtain inter-component information. Furthermore, there is no need to know the exact composition of components in the sample, as it is the fluorescence finger-print rather than the components of the sample that is detected. If so desired, in a specific application, it may be possible to give a chemical characterisation of the information used by the classification system. It may even in certain situations be possible to do so directly from the mathematical parameters derived from the physical parameters.

For one sample normally more than several thousand data variables are obtained, and the amount of data increases by the number of samples used but the number of data variables is constant for each sample. In prior art it was common practise to discard most of the spectrofluorimetric information and use but a few selective or semi-selective physical parameters but the present invention makes use of all available information.

By the present invention is has become possible to obtain information regarding an animal or a human being by subjecting a biological sample from said animal (human being) to a fluorescence analysis. Examples of the information provided by the present invention may be any information regarding health condition, such as information regarding presence/absence of a specific disease, group of diseases or risk of later attaining a specific disease or a body condition, or concentration of a specific compound or medicine.

In a first aspect the invention relates to a method of training a classification system for characterising a biological sample. It is the purpose of the training that a classification system is obtained, said system holding enough information to be used for characterising an un-classified and unknown biological sample into one of the classes of the classification system. By the term unknown is meant a sample for which no characterisation information is known.

It is also the purpose of the training of the system that this training incorporates a validation that substantiates how well classification can be performed on specific samples in the future as well as improving the validation specificity and sensitivity over time.

Samples

The biological sample may be any sample suitable for fluorescence analysis. The sample may be fluid or solid, as is appropriate. It is an object of the present invention to acquire the necessary information from the sample using as few pre-treatments as possible, preferably without any pre-treatments as such.

Accordingly, in a most preferred embodiment the sample is transferred directly from the animal or human being to be subjected to fluorescence analysis, in order to obtain data relating to fresh, un-treated samples. In case it is not possible to use the biological sample directly, it may be stored, for example by freezing the sample.

A characteristic of the biological sample is that it is preferably not directly related to the specific conditions, in that the spectroscopy is preferably not conducted on the tissue suspected to express the disease, whereby it is often possible to diagnose a condition or a disease in a easy manner, since the biological sample to be examined may be easily established, such as a urine sample or a plasma sample.

Fluid samples may be any fluid samples obtainable from animals or human beings, i.e. body fluids, such as biological samples selected from blood, plasma; serum, saliva, urine, cerebrospinal fluid, tears, nasal secrete, semen, bile, lymph, milk, sweat and/or faeces.

In a preferred embodiment the fluids are easily available fluids, such as urine samples, milk, blood and/or serum and/or plasma samples. Most preferred are urine, milk or saliva samples or any other samples that are obtainable without any invasive technique.

The fluid sample is subjected to fluorescence analysis without drying, and preferably without any other changes in concentration, such as separation and enrichment. The fluid sample may be arranged in a sample compartment being closed or open before exposing the sample to excitation light.

It is however also possible with the present invention to use tissue samples, such as solid tissue samples directly. Examples of tissue samples include hair and nails. The tissue sample may be any sample, such as a biopsy of tissue, that is subjected to fluorescence spectroscopy. In the present invention the tissue is not directly related to the specific condition(s), thus the term "the tissue sample is not associated with said condition(s)" means that for example when classifying with respect to cancer the tissue sample does not represent the possibly cancerous tissue, but tissue from another part of the individual.

The biopsy may be from any tissue, such as from muscle, cutis, subcutis, kidney, brain, and liver.

The solid samples may be classified on the solid form, but it may often be necessary to provide a liquid form of the tissue before subjecting the sample to fluorescence spectroscopy. The liquid form of the tissue may be obtained by dissolving the tissue or mechanically destroying the tissue, such as blending the tissue, to obtain a suitable liquid suspension of the tissue.

Furthermore, it is possible to use a sample positioned in situ or non-invasive, i.e. not removed from its normal environment. The sample does not need to be physically removed from its place in the animal or human being. The invention also encompasses the possibility of in situ analysis of samples. This can be done easily with samples like skin, hair, and nails, but it is likewise possible to conduct the excitation and fluorescence light beams by means of light guides to and from the liquid or tissue samples within the body. This may be accomplished by conducting the measurements transdermally. The light guides may thus be introduced into the body via body openings, such as the mouth, nose, ears, rectum, vagina, or urethra, or the light guides may be introduced through the blood vessels or inserted directly into tissue. In this way various fluids may be measured in situ, as well as some of the solid tissue samples. In a preferred embodiment the biological sample is selected from body fluids, hair and nails, more preferred from body fluids.

Excitation Light

The physical parameters may in principle be obtained for a wide variety of excitation light wavelengths. The wavelengths are preferably selected to be within the range of from 100 nm to 1000 nm, such as from 100 to 800 nm, more preferably within the range of from 200 nm to 800 nm, such as from 200 nm to 600 nm.

Normally several wavelengths are used, such as from 2 to 10.000, 4 to 10.000, 2 to 1000, 4 to 1000, 2 to 100 wavelengths, such as from 4 to 100 wavelengths, for instance 2–30, such as from 4 to 30 wavelengths, such as 2–10, such as from 4 to 10 wavelengths, for instance 2–6 wavelengths in order to describe an excitation-emission matrix optimally. Sets of wavelength may be chosen so that each wavelength differs from the other by at least 01 nm, such as at least 0.5 nm, for instance at least at least 1 nm, such as at least 5 nm, for instance at least 10 nm, such as at least 50 nm, for instance at least at least 100 nm, such as at least 150 nm, for instance at least 250 nm, such as at least 500 nm, for instance at least 600 nm, such as at least 700 nm, and at most 750 nm.

Multiwavelength excitation may be established either sequentially by varying the setting of a monochromator or other dispersing or filtering device in front of a continuous lightsource like a xenon lamp. Alternatively, the sample may be exposed to the full spectrum of a continuous light source equipped with a polychromator which disperses the light spatially. Thus, different zones of the sample are exposed to exciting light of different wavelengths. Furthermore, an array of single wavelength light sources light e.g. lasers or light guide bundles may be used either in the sequential mode or in the spatially separated mode.

Accordingly, at least 2 excitation light wavelengths are selected such as at least 4, at least 6, at least 8, at least 10, or more. The excitation light of each wavelength may be used simultaneously or sequentially. In a preferred embodiment 4 wavelengths are selected, such as excitation light having a wavelength of 230 nm, 240 nm, 290 nm, and 340 nm. Each sample is then subjected to excitation light of each wavelength. In another preferred embodiment 6 wavelengths are selected.

The predetermined excitation light wavelength(s) is provided by use of light sources as is known to a person skilled in fluorescence spectroscopy.

Emission

The determination of the various physical parameters is done by equipment known to the person skilled in the art.

In fluorescence spectroscopy emission light intensities at different wavelengths are recorded for each excitation light wavelength. Preferably the emission light is sampled with 0.5 nm intervals or 1 nm intervals. Thereby a matrix of excitation-emission data is obtainable for each sample. Normally the spectral distribution of light emitted from the sample is ranging from 200 nm to 800 nm.

The emitted light is detected by any suitable detector, such as a one-dimensional detector, for example a photomultiplier. Alternatively, a scanning camera, a diode array, a CCD or a CMOS, all in principle being viewed as a two-dimensional array of several thousand or more detectors. The intensity of the light is detected on each detector thus permitting the whole spectrum or the whole EEM to be obtained in a single electronic measurement.

The emitted light from the samples may be focused onto the detectors by means of conventional focusing systems, as well as passing through diaphragms and mirrors.

Physical Parameters

Most frequently the physical parameter to be determined in order to perform a data analysis is the intensity as a function of excitation wavelength and/or the emission wavelength. However, any other information contained in photoluminescence may be obtained from the sample such as fluorescence lifetime, phosphorescence intensity, phosphorescence lifetime, polarisation, polarisation lifetime, anisotropy, anisotropy lifetime, phase-resolved emission, circularly polarised fluorescence, fluorescence-detected circular dichroism, and any time dependence of the two last mentioned parameters.

Fluorescence intensity is easily measured at room temperature, and may therefore be chosen for many of the samples. Furthermore, a great number of organic natural products are known to be fluorescent. Phosphorescence may, however, also be performed at room temperature.

Luminescence lifetime in general, as well as phosphorescence lifetime are defined as the time required for the emission intensity to drop to lie of its initial value.

When using phase resolved fluorescence spectroscopy it is possible to suppress Raman and scattered light, leading to very good results for multicomponent systems.

In luminescence polarisation measurements, conventional spectra are obtained by scanning excitation spectra and measuring intensity parallel and perpendicular to the polarisation of exciting light. The polarisation may be calculated as the ratio of the difference of the two measurements to the sum of the two measurements. The anisotropy parameter is obtained by multiplying the perpendicular intensity by two in the denominator sum of this ratio.

Processing

The detectors are preferably coupled to a computer for further processing of the data. The physical parameters measured or determined by the detector are processed to a form suitable for the further mathematical calculations. This is done by allocating data variables to each physical parameter determined, thus obtaining data variables related to the physical parameters, The physical parameters determined are often subjected to a data analysis through the data variables, such as a oneway matrix of spectral information, a two-way matrix of spectral information, a three-way matrix of spectral information, a four-way matrix of spectral information or, a five-way or higher-order matrices of spectral information.

Characterisation Information

To obtain information relating to a specific condition in the animal or human being it is of importance that the data relating to the spectra obtained are correlated to characterisation information regarding the same biological sample. The information regarding the biological sample is preferably obtained substantially simultaneously with the biological sample, however, for characterisation data not varying essentially it is sufficient to obtain the data after having obtained the physical parameters.

The characterisation information relates to the classes intended to be generated through the training period.

The characterisation information is for instance relating to the presence or absence of a physical condition, such as a specific disease, or information regarding smoking, drinking, abuse of drugs, nutritive condition, etc. Furthermore, the characterisation information may include information such as sex, race, age or the like that is relevant for the classification. The characterisation information may also be information regarding responsiveness to a treatment as well as information regarding side effects of a treatment. The characterisation information may give information of both qualitative and quantitative information.

Also predictive information regarding an individual's risk of acquiring a condition or disease may be obtained by the present invention. The training of the system may be conducted by subjecting a kohorte of individuals to successive sample analysis and classify the samples into groups of individuals acquiring the disease and groups staying healthy during the period of sampling.

The characterisation information must be correlated to the spectral information obtained from the sample, in order to obtain the trained system ready for testing unknown samples.

Validity

Each sample is subjected to fluorescence spectroscopy before the data analysis is performed in the training of the classification system. The sample may be one sample from each animal or human being, or several samples from the same individual, each sample obtained at a different time interval or from different fluids or from different instruments.

Depending on the classes to be identified when training the classification system it is of importance to train the system with a sufficient number of samples. The determination of the sufficient number of samples is primarily determined by the similarity of the fingerprints of different classes. Indirectly, this can often be related to the number of expected latent variables, wherein the latent variables are weighted averages of the data variables. It is preferred that the ratio of number of training samples to the expected number of latent variables is at least 5:1, preferably at least 10:1. More preferred the ratio is 50:1, and even more preferred 100:1. The more training samples, the more reliable a system. Training is a continual improvement of the system and any sample is also a training sample being weighted decreasingly, however, over time.

The samples being classified in each class are preferably a representative group of samples to allow the most reliable classification, wherein representative is meant to mean exhibiting all variations influencing said classification. These variables can for example be age, sex, medication, existing disease, and race to match the population for which the classification system is designed.

Mathematics

A central aspect of the, invention is the performance of a multivariate analysis, whereby the data variables relating to the physical parameters are evaluated and model parameters are obtained. The model parameters describe the variation of the data variables. Thereby the samples are classified uniquely into classes. The identification of the classes is obtained when each sample is correlated to the characterisation information relating to said sample. Correlation in this respect is not necessarily a mathematical correlation. Correlation in this respect may also comprise the possibility of performing a comparison of data or fluorescence spectra.

Preferably, the model parameters are latent variables being weighted averages of the data variables.

The identification of the belonging to a class is obtained when the data variables of a sample are input to a trained classification system yielding either qualitative and/or quantitative information as to whether a sample belongs to a class.

In performing the data analysis it is often an advantage that the characterisation information is already available. Thereby it becomes possible to detect exactly those structures in the data that are relevant for detecting the difference between the classes and not just structures that may not be relevant for the classification.

The multivariate statistical methods suitable for the present invention are for example represented by chemometric methods like principal component analysis (PCA), partial least squares regression (PLS), soft independent modelling of class analogy (SIMCA) and principal variables (PV).

A non-exclusive list of other multivariate statistical methods include: Principal component analysis[14], principal component regression[14], factor analysis[2], partial least squares[14], fuzzy clustering[16], artificial neural networks[6], parallel factor analysis[4], Tucker models[13], generalized rank annihilation method[9], locally weighted regression[15], ridge regression[3], total least squares[10], principal covariates regression[7], Kohonen networks[12], linear or quadratic discriminant analysis[11], k-nearest neighbors based on rank-reduced distances[1], multilinear regression methods[6], soft independent modeling of class analogies[8], robustified versions of the above and/or obvious non-linear versions such as one obtained by allowing for interactions or crossproducts of variables, exponential transformations etc.

The term "describing the variation of the data variables" means that the latent variables retain the relevant information regarding the variation, whereas "noise" is preferably not giving any significant part in the latent variables.

As an example of a multivariate data analysis technique, the use of principal component analysis—PCA—will be outlined [Jackson 1991] as this technique will be used in the following exemplary applications. An I×J data matrix, $X \in \Re^{I \times J}$, is given where I is the number of rows (samples) and J is the number of columns. The number of variables will typically exceed the number of samples by far. This poses the practical problem that the matrix is typically ill-conditioned. Thus, any traditional analysis using the whole set of raw data will lead to useless results due the numerical problems involved in handling the large amount of data.

Using PCA, the original J variables are replaced by F (<<J) latent variables which, in this case, are also called principal components. These latent variables are found as weighted averages of the original variables in such a way that they provide the best possible description of the data in a least squares sense. Each latent variable consists of a score vector t (I×1) and a loading vector p (J×1). The loading vector is constrained to norm one and the score vector is found by regressing X onto p $$t = Xp/p^T p = Xp$$

For the first latent variable it holds that it minimizes $$\|X - tp^T\|_F^2$$

where $\|\cdot\|_F^2$ denotes the squared Frobenius norm. Thus, the first latent variable provides the least squares best-fitting rank-one model of X. The second latent variable is found under the constraint that the second score vector $t_2$ is orthogonal to the first score $t_1$ and that second loading vector $p_2$ is orthogonal to the first loading $p_1$. Under this restriction, the second latent variable is found such that it provides the best possible fit to the data. Extracting F such components will yield a rank F model of the data. Let the score matrix T (I×F) hold the score vectors $t_f$, f=1, ..., F and the loading matrix P (J×F) holds the loading vectors $p_f$, f=1, ..., F of this solution. It then holds that T and P provide the solution to $$\operatorname*{argmin}_{G,R} \|X - GR^T\|_F^2$$

and thus provide the best-fitting rank F solution. In practice, the solution to this problem can be found using a truncated singular value decomposition of X. If $U_F$ holds the first F left singular vectors, $V_F$ holds the first F right singular vectors and $S_F$ is an F×F diagonal-matrix holding the first F singular values in its diagonal, then it holds that $$T = U_F S_F;\ P = V_F.$$

In order to choose the appropriate number of components, F, several strategies are possible. One approach is to use cross-validation [Wold 1978] in which elements are left out of the data in turn. For each set of elements left out, a model is fitted to the remaining data and the model $$\hat{X} = TP^T$$

is used to estimate the left out elements. After all elements have been left out once, the thus obtained residuals are used for calculating the predicted residual sum of squares (PRESS) and the number F for which PRESS is at its minimum is usually taken to be the appropriate number of components. For exploratory purposes, it is usually sufficient to simply retain the first 2–5 components because these, per definition, retain most of the variation in X. It is noted that if cross-validation is to be performed in this way, special algorithms have to be used because of the missing values in the data [Grung & Manne 1998].

The practical usefulness of PCA arises because of the information preserving compression of the data based on the empirical observations rather than on theoretical derivations. The scores T can be seen as the coordinates of X in the reduced space defined by the truncated basis P and the latent variables therefore provides a condensation of the original J variables into F new ones. This condensed representation is feasible because it allows a holistic visualization of the structure in the data and because it makes it possible to do quantitative analysis such as regression and classification in a straightforward way.

In some situations, the interest is to specifically make a quantitative model relating multivariate data to one or more responses by a regression model. This way, it is possible to measure future samples by the multivariate approach and then predict the response from the regression model. Such a regression problem suffers from the same problems as outlined above and for the same reason rank-reduced regression is often employed. As an example of such, the partial least squares regression—PLS—method will be described.

As before a multivariate set of data X (I×J) is available and further a response vector y (I×1) is given. More responses can be handled as well, but this is not pursued here. The aim is to find a regression vector b that provides a feasible solution to the regression problem $$y = Xb + e$$

where e (I×1) is a vector of unmodelled residuals. Using multiple linear regression (J≤I) or similar approaches, it is possible to obtain a minimum variance unbiased estimate of b but due to the constraint of being unbiased, the variance will, in practice, make the estimate useless for predictions in the situations considered here [de Jong 1995, Martens & Naes 1987, Wold et al. 1984]. Instead, a regression vector is sought that yields a low mean squared error, hence relaxing the restriction of being unbiased focusing on low total error. In PLS, this is achieved by extracting components sequentially such that each extracted score vector has maximal covariance with the yet unexplained variation in the response [Bro 1996, Martens & Naes 1989]. Usually X and y are centered by subtracting the column average from each column, thereby removing possible offsets. For centered X and y, the first component is determined by defining a weight vector as $$w = \frac{X^T y}{\|X^T y\|_F}.$$

From this vector, the score vector t is defined as $$t = Xw$$

and finally a loading vector p is defined as $$p = X^T t / t^T t.$$

The rank-one model of X is then given by $tp^T$ and the regression model relating the bilinear model of X to y is defined by the scalar $$r = y^T t / t^T t.$$

giving the initial prediction of y as tr. The model of X ($tp^T$) and the prediction of y (tr) are subtracted from X and y and the following component is determined similar to above but using the residuals of X and y as input. After calculating F components in this manner, the following matrices and vectors are given: T (I×F), P (J×F), W (J×F), r (F×1). The regression vector can then be determined as $$b = W(P^T W)^{-1} r.$$

As for PCA, cross-validation is usually employed to determine the optimal rank of the model with the only difference being that whole samples are excluded in each cross-validation segment, and the residual error determined is the response error.

Other Variables

The classification system may be obtained on the spectral information only. However, in some situations it may be appropriate to incorporate other variable(s) in the multivariate analysis.

These other variables may be variables relating to the sample supplying the spectral information or they may be variables that compensate for a specific condition of the sample.

Examples hereof may be the measurement of pH, electrolytes, temperature in the sample before subjecting it to spectroscopy, clinical parameters. Thereby variations in the other variables may be compensated for in the final classification.

In another embodiment other variables are variables relating to the animal, including a human being, to be characterised. Non-exclusive examples of these variables are hair colour, skin colour, age, sex, geographic origin, affiliation, prior diseases, hereditary background, medication intake, body conditions (such as e.g. surgery), stress level, medical diagnoses, subjective evaluations, and other diagnostic tests (e.g. immunoassays, x-ray diagnosis, genomic information or an earlier chemometric test).

Pre-Treatment

It is an advantage of the present invention that no pre-treatment of the sample is normally necessary.

However, for some of the samples or applications it may be necessary or convenient to perform an adjustment before subjecting the sample to spectroscopy.

Examples of pre-treatment may be adjustment of pH of the sample to a predetermined value, or heating or cooling the sample to a predetermined temperature. The sample may be treated with chemicals (complexing agents etc.) in order to develop e.g. fluorescent complexes involving inherent non-fluorescent molecules in the sample.

Other types of pre-treatment include addition of chemical substances, measurement under a gradient imposed by varying additions of chemical substances, simple chromatographic pre-treatments based on either chemical or physical separation principles.

Classification System

Another aspect of the present invention is the classification system for characterising a biological sample into at least one predetermined class.

When the classification system has been trained as discussed above, it is ready for classifying samples with unknown characteristics. The classification system preferably comprises the following components:

a) a sample domain for comprising a biological sample, b) light means for exposing the sample to excitation light in the sample domain, c) a detecting means recording the physical parameter(s) of light emitted from the sample, d) optionally computing means for performing data handling of the physical parameters, obtaining data variables, e) optionally processing means for providing model parameters from data variables of the sample, f) at least one storage means for storing physical parameters and/or data variables and/or model parameters of the biological sample, g) at least one storage means for storing physical parameters and/or data variables and/or model parameters and characterisation information of a trained classification system, h) means for correlating physical parameters and/or data variables and/or model parameters from the sample with physical parameters and/or data variables and/or model parameters of the trained system, and i) means for displaying the characterisation class(es) of a sample.

The sample domain may be a sample chamber for accommodating a container with a liquid, a solid or a semi-solid sample. However, the sample domain may also be a domain in the individual to be classified in that the analysis can be performed on a sample in situ such as in the blood vessels or on the superficial body parts such as skin, nails, or hair.

The classification system may be provided as a whole unit, wherein the spectroscopy of the sample is conducted by the same unit from where the data relating to the characterisation classes of the sample is displayed.

It is however contemplated within the scope of the present invention, that the system is comprised of at least two units, wherein one unit is performing the steps a) to f), arid another unit is performing the steps g) to i), Other units comprising other parts of the system are also contemplated, such as one unit performing the steps a) to d) and storage means for storing physical parameters and/or data variables from f) or a) to g), and the other unit comprising the rest of the parts. Yet another unit comprises steps a) to c) in one unit and the remaining steps in the other unit.

By the system thus divided into at least two units, it is possible to obtain the spectroscopic information from a wide variety of decentral locations and perform the processing centrally. The data or the classification system may then be transmitted by any suitable means, such as conventional data transmission lines, for example the telephone lines, or via internet or intranet connections.

This facilitates the use of the classification system since any physician may provide the biological sample, have it subjected to spectroscopic analysis at his or her clinic and have the data correlated decentrally without the need of being capable of conducting this processing. The physician may then call the central unit to request the correlation and classification of the sample data. Depending on the transmission mode and equipment, the result may be displayed on a screen or printed on paper, or informed by telephone.

In addition to the result, other information may be provided, such as information regarding sample errors, for example the test requires a urine sample not a serum sample, information about the statistics, such as fuzziness, the degree of membership of a group, power and significance.

Diagnosis

In principle the classification system trained according to the invention may be used to characterise any biological sample with respect to any kind of information.

Interesting parts of the present invention relate to the possibilities of diagnosing a condition or the risk of acquiring a condition, such as a physical condition in an animal or a human being, from a spectrofluorimetric analysis of a biological sample from said animal or human being and relating the spectroscopic data with data in the classification system.

As for any other diagnostic tool, the present invention provides a diagnostic tool, that may give a strong indication of a disease or condition or a risk of such disease or condition, but for many of the diagnosis these may have to be confirmed by more specific diagnostic methods, more precisely directed to the specific diagnostic area. However, due to the simplicity of the present invention, the precise diagnosis may be obtained faster and much more cost-effective than by hitherto known methods.

The disease detected may be any disease that provides combination of components in the biological sample that is detectable as a pattern by the fluorescence spectroscopy.

Thus the disease may be selected from any official disease classification system, such as ICD-9/10 (WHO's official international classification list), ICIDH-2 (International Classification of Functioning and Disability) but not limited to those two. Such classification system includes at least the following groups (the numbers in brackets refer to the ICD 9 list) of human diseases as well as similar diseases related to other animals:

Infectious and parasitic diseases (001–139)

Neoplasms (140–239)

Endocrine, nutritional and metabolic diseases, and immunity disorders (240–279)

Diseases of the blood and blood-forming organs (280–289)

Mental disorders (290–319)

Diseases of the nervous system and sense organs (320–389)

Diseases of the circulatory system (390–459)

Diseases of the respiratory system (460–519)

Diseases of the digestive system (520–579)

Diseases of the genitourinary system (580–629)

Complications of pregnancy, childbirth, and the puerperium (630–677)

Diseases of the skin and subcutaneous tissue (680–709)

Diseases of the musculoskeletal system and connective tissue (710–739)

Congenital anomalies (740–759)

Certain conditions originating in the perinatal period (760–779)

Injury and poisoning (800–999)

The sample may be classified to belong to a class for any of the diseases above, quickly leading the examining physician to the most likely diagnosis. The sample classification may be confirmatory or it may have to be confirmed by more specific diagnostic tools.

Furthermore, the sample may be classified into more than one class, whereby a more refined diagnostic tool is provided.

For many of the diseases mentioned above, it is of utmost importance that an early diagnosis is obtained, but many of these diseases may be difficult to diagnose conventionally at the early stage due to very discrete symptoms. By the present method it is possible to get a dear indication of the disease at an early stage.

Furthermore, by the present invention it may furthermore be possible to reveal individuals susceptible to a specific disease, due to the classification of relevant biological samples from these individuals.

In particular in respect of cancer, the invention may be used to classify different forms of cancer, including cancer in various organs. Thus, the invention may be used to diagnose renal cancer from colon cancer for example. Futhermore, different stages of a cancer may be diagnosed, including precancerous stages. Furthermore different cancer aggressivity may be diagnosed for example the invention may identify high-risk cancer patients independently of whether the underlying cancer is anatomically localised in for example breast, lung or colon.

It is likewise conceivable that the present invention can be used for screening of individuals to identify those suffering from a particular disease or those being susceptible to a disease or those expected to suffer from the disease in the near future.

Also, the present invention may reveal individuals at risk due to environmental hazards, job environment or the like.

The present invention may also be used to diagnose a variety of abuse of medicine and/or narcotics, for example in relation to control, or in un-conscious or semi-conscious individuals that have to be treated for their abuse.

Another aspect of the invention may be to detect physical and/or psychological stress in an individual, and thereby detect persons at risk of acquiring stress related diseases.

Yet another aspect of the invention may be the detection of genetic modifications or inherited risk by examining a biological sample by fluorescence spectroscopy.

Yet another aspect of the invention may be to provide a quantitative answer to the degree of any of the above-mentioned situations (e.g. the amount of medicine, the degree of risk etc.).

In a further embodiment the invention may be used as a tool for predicting the responsiveness to a specific treatment for an individual suffering from a particular disease. For example the invention may be used to classify individuals suffering from cancer into classes of predicted responsiveness to chemotherapy, radiations and/or operation. Another example may be to predict the useful medication of depressive individuals.

EXAMPLES

Example 1

Example of the Use of Multidimensional Sensorial Fluorescence Data Analysis

Smokers/Non-Smokers Data

This example illustrates the usefulness of training a classification system on a small experimental data set. The data set comprises 18 samples taken from 14 individuals.

Sampling and Measurements

Urine was collected from several male persons and measured spectrofluorimetrically. Approximately half of the testees were smokers, the other half non-smokers. Some samples were measured the same day, others up to 4 days after sampling. The samples were kept at −4° C. until measurement was performed. The urine was not diluted before measurement. Fluorescence spectra were recorded on a Perkin-Elmer LS-50B spectrofluorimeter using front face illumination.

Scanning was performed from excitation wavelengths 230 nm to 500 nm and from emission wavelengths 268 nm to 900 nm.

Data Handling

For each thus obtained fluorescence landscape, the obvious non-bilinear parts (emission below excitation and zero- and first-order Rayleigh scatter) were removed and the corresponding elements denoted 'missing'. This lead to data of the type shown in FIG. 1.

For each sample, i, a matrix $X_i$ is thus obtained of size J×K with J being the number of emission wavelengths and K being the number of excitation wavelengths. The whole data set is arranged in a three-way tensorial structure with typical elements $X_{ijk}$, i=1, . . . , I, j=1, . . . , J, k=1, . . . , K. This three-way structure may, geometrically, be interpreted as a box of data, where each horizontal slice corresponds to a specific sample, each vertical slice corresponds to a specific emission wavelength, and each frontal slice corresponds to a specific excitation wavelength.

In the following, this three-way tensorial array is matricized, i.e. rearranged into a two-way matrix called Z where each row corresponds to a sample, and holds all combinations of excitation and emission. In this setup—interpreted as in ordinary multivariate data analysis—there are 4003 variables (plus a fraction that is removed because it contains either variables which are set to missing or variables with extremely small variance).

Data Modelling

This data matrix is subjected (Matlab, version 5.2) to principal component analysis, in which the 4003 data variables are replaced with three latent variables. These latent variables are weighted averages of the original data variables, defined so that the projection of Z onto the space spanned by these, retain as much variation as possible. That is, the latent variables T of size 18×3 are defined through a set of weights, P (4003×3) as the solution to $$\max_P \|ZP(P^T P)^{-1} P^T\|_F^2$$

where $\|\mathfrak{R}\|_F$ denotes the Frobenius norm. Because the weight matrix is chosen to be orthogonal (without loss of generality), this expression can be reduced to $$\max_P \|ZPP^T\|_F^2$$

From this expression, the latent variables T are found as the coordinates of Z in the reduced space defined by the truncated basis P $$T = ZP.$$

Note, that the latent variables are found using no information about the status of the persons (smoker or non-smoker). The latent variables provides a condensed picture of the original 4003 variables, and a simple graphical representation of these is sufficient to illustrate the power of this compression (FIG. 2).

As can be seen in the plot, all non-smokers fall above the dashed line and all but one smoker falls below the dashed line. Disregarding for now the one outstanding sample (S3), it is easily seen that this simple plot provides a powerful tool for assessing whether a person is a smoker or not. Simply by measuring the fluorescence excitation-emission data from a urine sample, and projecting the obtained data onto the factor weights found above, a set of scorings on the three latent variables is obtained for a new person. When these are plotted in the above plot, the position of the sample above or below the dashed line enables an assessment of whether the person is a smoker or not. In fact, the sample of the person identified as S2 in the lower right part, was left of the initial analysis and only positioned after the plot was generated. As can be seen the position is correctly below the dashed line, indicating that the person is a smoker. This graphical assessment can be automated in a number of ways using appropriate pattern recognition techniques.

The one smoker-sample located above the dashed line indicates an erroneous condition. However, in this initial feasibility study, no detailed information on the individual persons were available nor of their smoking habits. Hence, there can be numerous reasons for this particular position, such as the person had not been smoking that particular day and the day before etc.

Example 2
Detecting Fasting Condition

A patient undergoing a surgical procedure in general anesthesia is exposed to a relatively high risk if he or she has being eating or drinking before becoming intubated. Under a planed procedure the patients have been instructed not to indigest before the surgical procedure. However, the patients (especially children or elderly persons) will not always refrain from indigesting. In both the planed and acute procedure it is of help for the physician to know whether a patient has been eating or not. Thus, such a test will be a feasible 'add-on' to other tests with low marginal cost.

Samples and Solutions

This study includes 9 normal persons fasting and 14 normal persons not fasting. The conditions for all 23 persons were identical except for the question of whether the persons had been fasting or not.

For each person a blood sample was taken and blood plasma therefrom frozen. The blood plasma samples were defrosted and measured at room temperature. The samples were measured undiluted front face in a 1 mm cuvette on a Perkin Elmer LS50B (Copenhagen University). The excitation wavelength interval range was 230–400 nm (10 nm steps) and the excitation and emission slits were 4 nm and 3 nm, respectively. The scan rate was 1000 nm/min. In all, a total of 3834 variables were measured for each sample. At each excitation wavelength, the emission was removed in the range from 250 to 22 nm above the excitation wavelength in order to remove Rayleigh scatter and other irrelevant phenomena [Bro 1998, Bro. 1999]. Upon removal of these variables, a total of 2020 variables were retained. A typical landscape is shown in FIG. 3.

Results

Figure 4:
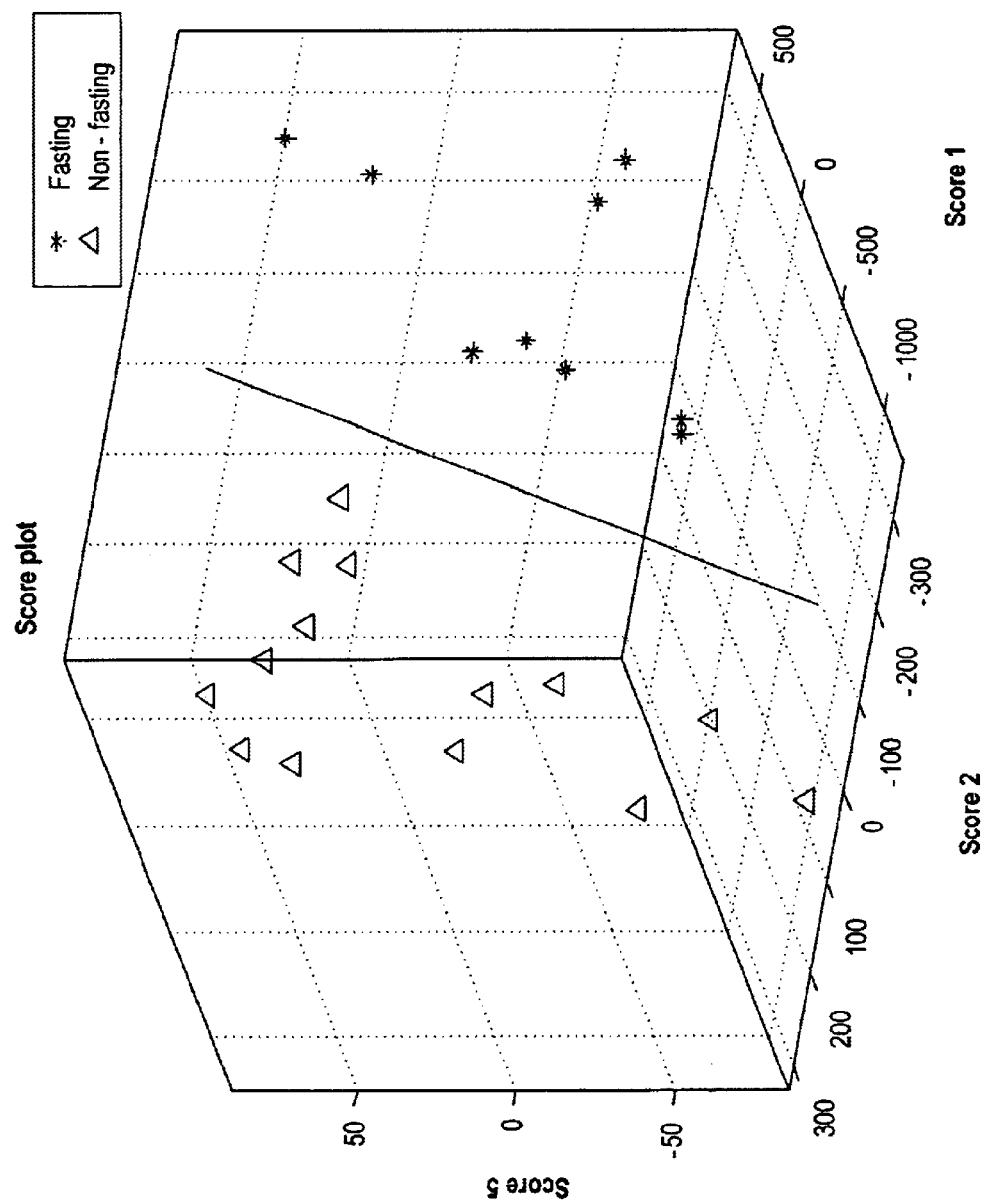

The data were fitted by a PCA model. The model indicated that at least up to six components contained valid information. For the present purpose, it means that the main systematic part of the fluorescence variation is retained in these six new variables. A resulting score plot is shown below (FIG. 4). It is a three-dimensional scatter plot of score one, two and five. Each plot represents the relative position of one person with respect to that persons fluorescence fingerprint. It is immediately seen in the plot that all fasting persons appear to the right in the plot and all non-fasting persons appear to the left.

The significance of this particular plot can be described as follows. In estimating the six components in the PCA model, no use whatsoever has been made of the fasting-information. The PCA model is only based on the fluorescence data. The empirical observation that it is possible to assign areas of the plot to only fasting persons and areas to only non-fasting persons means that a discrimination between the two groups has been achieved. Thus, for a person where it is unknown whether the person is fasting, it is possible to measure a corresponding fluorescence landscape under similar conditions and thereby obtain the scores for that particular person. Inserting these scores in the plot above, it is then possible to evaluate or verify whether the person is fasting or not by simply monitoring to which side of the indicated line the point is positioned.

More elaborate decision rules can easily be envisioned using e.g. linear discriminant analysis [Indahl et al. 1999], SIMCA [Wold & Dunn, III 1983] or some similar classification approach. However, for this feasibility study it suffices to show that discrimination is possible to achieve with multivariate analysis of fluorescence landscapes.

Example 3
Analysis of Colon Cancer Data

Having a simple tool for detecting colon cancer is a very interesting application of the current invention.

Materials and Methods

The data gathered here, include 77 samples (9 normal persons; 13 with benign tumor; 11 Dukes A; 14 Dukes B; 15 Dukes C; 15 Dukes D). For each person a blood sample was taken and blood plasma therefrom frozen. The blood plasma samples were defrosted and measured at room temperature. The samples were measured undiluted front face in a 1 mm cuvette on a Perkin Elmer LS50B (Copenhagen University). The excitation wavelength interval range was 230∝400 nm (10 nm steps) and the excitation and emission slits were 4 nm and 3 nm, respectively. The scan rate was 1000 nm/min. In all, a total of 3834 variables were measured for each sample. At each excitation wavelength, the emission was removed in the range from 250 to 22 nm above the excitation wavelength in order to remove Rayleigh scatter and other irrelevant phenomena [Bro 1998, Bro 1999]. Upon removal of these variables, a total of 2020 variables were retained.

Results

For each class of samples, a principal component analysis (PCA) model is fitted to the fluorescence data. This is important for exploring the homogeneity of the group and for eliminating obvious erroneous samples.

As an example, a PCA model of the data of persons with benign tumors is discussed. In this group, there seems to be several individuals located distinctly isolated (4490, 4499, 8319, 4506) in the score plots (FIG. 5). The remaining persons are situated in the same group in the score plot. The reasons for the behavior of the outlying samples can be related to the patients (extreme patients in some sense), to the sampling of the blood (extreme sampling in some sense) or to the actual measurements. For e.g. 4490 the person was later found to be incorrectly classified as benign. For 4506 the technician noted that the suspension was cloudy indicating incorrect treatment of the sample. For 8319 the sample was noted to have precipitated matter, whereas for 4499 no reason was found for its behavior, besides the outlying behavior of the measured fluorescence data. In order to assure that the subsequent results are as robust as possible, the four samples were excluded; the three because of erroneous sample treatment or measurement and the fourth because of assumed but unknown erroneous sample treatment or measurement.

Similar outlying samples were found in other groups as well. E.g. for the group of Dukes A one sample had a very different fluorescence pattern and was excluded. For the Dukes B samples, four such samples were observed. For Dukes C only sample VB106 is moderately outlying. For Dukes D, sample VB76 is moderately outlying. All in all, 11 samples out of the 77 were excluded. An explanation of the erroneous sample treatment or measurement was found for most of these samples, which makes the decision to exclude these valid and reasonable. It must however, be borne in mind, that for five of the samples, there was no explanation found for the strange behavior. Hence, excluding these from the subsequent classification model is somewhat hazardous, because similar correct samples might be anticipated in real applications. Nevertheless, for the present feasibility study, the samples are considered as outliers of which the cause is presently unknown.

In order to quantify how well these data can be used for screening for cancer, the data were split up into two groups: Persons without cancer (18) and persons with cancer (48). A cross-validation was performed in the following way. One person was left out in turn and subsequently a PCA model was fitted to each group of data. Thus two PCA models were built. For the non-cancer group, five components were used and for the cancer group seven components were used. The data from the left-out person was subsequently fitted to the two independently obtained models yielding 1) a set of score values for the sample and 2) a set of residuals of fluorescence variation of that sample that the model could not explain. For one model, the score values of the new sample, t (1×F) and the scores from the calibration data T (I×F) are used for calculating the $T^2$ statistic as $T^2 = t(T^T T)^{-1} t$ and the Q statistic as $e^T e$ where e (J×1) is the vector of residual variation in the fluorescence data not explained by the model. The ratio of these values and the corresponding confidence limits obtained from the model are calculated (hence a value above one indicates that the sample is different). These two ratios are squared and summed and the square-root is used to test for class belongingness. If this number is less than the square-root of two, the sample is assigned to the class. If the sample is assigned to both classes, the one with the smallest number is the one chosen.

Using this approach the following classification result is obtained.

TABLE 1

Classification results

|  | Normal | Cancer |
| --- | --- | --- |
| Total | 18 | 48 |
| Correctly classified | 6 | 48 |
| Incorrectly classified | 12 | 0 |

It is observed that 82% are correctly classified and no false negatives are obtained.

Example 4

Fluorescence Measurements of Urine from Cardiac Patients

This example illustrates the treatment of outlying data and the ability of the invention to classify patients according to cardiac problems.

Samples

Eight urine samples were collected from seven men and one woman (post-menopause) who all were diagnosed with angina pectoris (samples #1–8). No other information was available from these patients. For comparison, urine samples were collected from five, arbitrarily chosen men (samples #9–13).

Measurements

Excitation-emission matrices were measured on the undiluted samples in a cuvette with 2 mm light path using front-face geometry on a Perkin-Elmer LS50B spectrofluorometer. In 28 consecutive scans the excitation wavelength was shifted in 10 nm steps from 230 to 500 nm. Emission intensity was recorded starting 20 nm after the excitation wavelength until two times the excitation wavelength minus offset (or 900 nm). Thus, neither first nor second order Rayleigh scatter were recorded. Emission intensity was measured in intervals of 0.5 nm. Spectral bandwidth on both monochromators was 5 nm. Scan-rate was 500 nm/min.

In total, fluorescence intensity was measured at 17828 different combinations of excitation and emission wavelengths and the values exported to Matlab, version 5.2.1.

Results

Although the data have a three-way structure (samples× excitation wavelength×emission wavelength) this is disregarded and the data are rearranged to a two-way structure (samples×combination of excitation and emission wavelength) as illustrated in FIG. 6. In this the 28 spectra, being arranged successively on an increasing wavelength scale, are displayed in an overlay fashion. The thus obtained two-matrix is centered by subtracting from each column its average value. By means of Principal Component Analysis this centered matrix is modelled by three principal components obtained from a singular value decomposition of the centered matrix.

An initial analysis reveals that patient #5 is quite extreme as compared to the remaining patients. This is illustrated in FIG. 7 in a so-called influence plot. In a two-component model patient five has a very large residual variation (upper left corner) whereas in a three-component model patient five has an extremely high leverage (lower right corner). This result shows that after two components most data are well described except for patient five. Consequently, in the third component the fifth patient gets a high leverage, which means that this patient is determining this component. This is a typical example of an extreme outlier. If the cause for the extreme behaviour is instrumental, the patient's data must be excluded as an incorrect measurement. If the cause is biological diversity, this diversity must be better represented in the data by incorporating more similar samples. As there are no further data in this specific investigation, the only suitable procedure is to exclude this sample.

Indirectly, the appearance of the outlying sample is an important illustration of one of the very important benefits of using exploratory data-analysis and having many physical parameters at disposal. Had it not been possible to detect the outlying sample, conclusions from the analysis could have been misleading. The model would be reflecting the difference between the samples as such and the extreme sample five, rather than explaining the inter-differences and patterns between all samples. The availability and. use of this evaluating tool during the model-building step shows that quality-deteriorating samples can be excluded, thus leading to improved models with improved validity.

Refitting the principal component model without sample five, a score-plot is obtained as shown in FIG. 8. Only the first two score vectors, PC1 and PC2, are displayed. The most important latent variables, PC1 and PC2 represent 97% of the original variation in the fluorescence data obtained in this investigation. The samples separate into two distinct clusters: Those below the dashed line in the lower left corner all represent samples from persons diagnosed with angina pectoris while the samples in the upper right corner all represent persons that are not diagnosed angina pectoris. Thus, it is clearly possible to separate diseased from healthy persons based on the fluorescence data alone.

It is indeed a significant finding, that the fluorescence data so clearly separate the two groups. Importantly, it is not merely the intensity of fluorescence that separates the patients. Differences in intensities are normally reflected in the first principal component of spectral data. In this case, however, the second component is also important for obtaining separation. In fact, the third component—not shown— also helps in obtaining further separation. This result indicates, that more subtle spectral components can be increasingly helpful in the discrimination between the groups.

As a larger data set becomes available the procedure outlined here will easily be formalised into a classification model that can identify persons with cardiac problems within a population of otherwise healthy individuals.

Example 5

Fluorescence Measurements of Urine Samples with Added Bacteria

The purpose of the example was to investigate if fluorescence spectra measured directly on urine samples correlate with different added levels of bacteria in the urine.

Samples

Seven urine samples spiked with $10^2$ to $10^8$ *E. coli* bacteria pr. ml and a control sample with no bacteria added. The eight samples were delivered by Alice Friis-Møller, Hvidovre Hospital and kept in a freezer until measurement.

Measurements

The samples were measured at front face at room temperature in a 2 mm cuvette on a Perkin Elmer LS50B (Copenhagen University). The excitation wavelength interval range was 230–400 nm (10 nm steps) and the excitation and emission slits were 4 nm and 3 nm, respectively. The scan rate was 1000 nm/min. The data were imported to Matlab using every $5^{th}$ emission wavelength giving a step of 2.5 nm in the emission scans. An important note is that the samples were measured in a sequence corresponding to the increase in bacteria content.

Results

Raw Data

The raw unfolded data are averaged with a factor 10 over the variables so the matrix dimensions become 8 samples× 384 variables. This corresponds to circa 25 nm steps in the emission scans. FIG. 9.

PCA

A PCA is performed on both the mean centered and the auto scaled unfolded spectral data. Variables with standard deviation of 0 and variables including missing values (NaNs) are excluded.

In FIGS. 10 and 11 the score plots from these models are shown. No large differences are seen between the auto scaled and the mean centered models.

PC1 clearly reflects the increase in bacteria content.

PLS Models

Mean centered PLS models with fluorescence spectra as the independent variables and the logarithm of the bacteria content ($10^2$ to $10^8$) as the dependent variable are developed.

It is observed that there is a strongly non-linear relationship between the spectra and the number of bacteria cells, but the function is monotone. (FIG. 12)

Conclusions

There seems to be a non-linear relationship between the spectra and the number of bacteria cells. This can be corrected for by some non-linear transformation of e.g. the dependent variable. Furthermore, it is important to note that the measurement order is crucial and should be randomised in a follow up study.

Example 6

Basic Fluorescence Measurements of Blood Plasma

The purpose of the example was to investigate the effect of dilution and pH on the fluorescence spectra measured on blood plasma. Both transmission and front face sample presentations were investigated.

Samples

A 10 ml pool of blood plasma samples from Hvidovre Hospital was produced. Samples were taken from this pool and diluted with 0.9% sterile NaCl, and the following dilutions were performed for front face:

| | |
|---|---|
| 1:2 | 3.5 ml pool + 3.5 ml NaCl (A) |
| 1:5 | 2.0 ml A + 3.0 ml NaCl (B) |
| 1:10 | 1.0 ml A + 4.0 ml NaCl (C) |
| 1:25 | 2.0 ml C + 3.0 ml NaCl |
| 1:50 | 0.5 ml B + 4.5 ml NaCl |
| 1:100 | 1.0 ml pool + 99.0 ml NaCl (F) |
| 1:200 | 2.5 ml F + 2.5 ml NaCl |
| 1:500 | 1.0 ml F + 4.0 ml NaCl |
| 1:700 | 1.0 ml F + 6.0 ml NaCl |
| 1:2000 | 0.25 ml F + 4.75 ml NaCl |
| 1:3000 | 0.20 ml F + 5.8 ml NaCl |
| 1:5000 | 0.10 ml F + 4.9 ml NaCl |
| and for trans- mission: | |
| 1:2 | 2.8 ml pool + 2.8 ml NaCl (A) |

-continued

| | |
|---|---|
| 1:5 | 2.0 ml A + 3.0 ml NaCl (B) |
| 1:10 | 1.0 ml A + 4.0 ml NaCl (C) |
| 1:25 | 2.0 ml C + 3.0 ml NaCl |
| 1:50 | 0.5 ml B + 4.5 ml NaCl |
| 1:100 | 0.25 ml pool + 24.75 ml NaCl (F) |
| 1:200 | 2.5 ml F + 2.5 ml NaCl |
| 1:500 | 1.0 ml F + 4.0 ml NaCl |
| 1:700 | 1.0 ml F + 6.0 ml NaCl |
| 1:1000 | 0.3 ml F + 2.7 ml NaCl |
| 1:2000 | 0.25 ml F + 4.75 ml NaCl |
| 1:3000 | 0.20 ml F + 5.8 ml NaCl |
| 1:5000 | 0.10 ml F + 4.9 ml NaCl |

Buffers were produced as follows:

pH circa 9: 0.1 M $NaH_2PO_4$ (1.785 g $NaH_2PO_4$ to 100 ml $H_2O$).

pH circa 4: 0.1 M $Na_2HPO_4$ (1.382 g $Na_2HPO_4$ to 100 ml $H_2O$).

pH circa 7: 1.379 g $NaH_2PO_4$+1.787 g $Na_2HPO_4$ to 100 ml $H_2O$.

pH circa 1: 0.1 M HCl (0.81 ml concentrated HCl to 100 ml $H_2O$).

and dilutions for the buffer experiment were:

| | |
|---|---|
| 1:2 | 2.0 ml pool + 2.0 ml buffer |
| 1:10 | 0.4 ml pool + 3.6 ml buffer (B) |
| 1:200 | 0.2 ml B + 3.8 ml buffer |
| 1:1000 | 0.1 ml B + 9.9 ml buffer |

All possible combinations of pH levels and dilutions were measured resulting in 16 (4×4) spectral landscapes. Both front face and transmission were tested.

Measurements

The samples were defrosted and measured at room temperature. The samples were measured in a standard 10×10 mm cuvette on a Perkin Elmer LS50B. The excitation wavelength interval range was 230–400 nm (10 nm steps) and the excitation and emission slits were 4 nm and 3 nm, respectively. The scan rate was 1000 nm/min. The data were imported to Matlab using every $5^{th}$ emission wavelength giving a step of 2.5 nm in the emission scans.

Results

Experiment 1: Dilution of Blood Samples Measured in Front Face Mode

Raw Data

In FIG. 13 examples of front face fluorescence spectra of an undiluted sample and the same sample diluted 1:5000 are shown. Very different spectral signals both with respect to intensity and shape are obtained for the two samples.

Figure 15B:
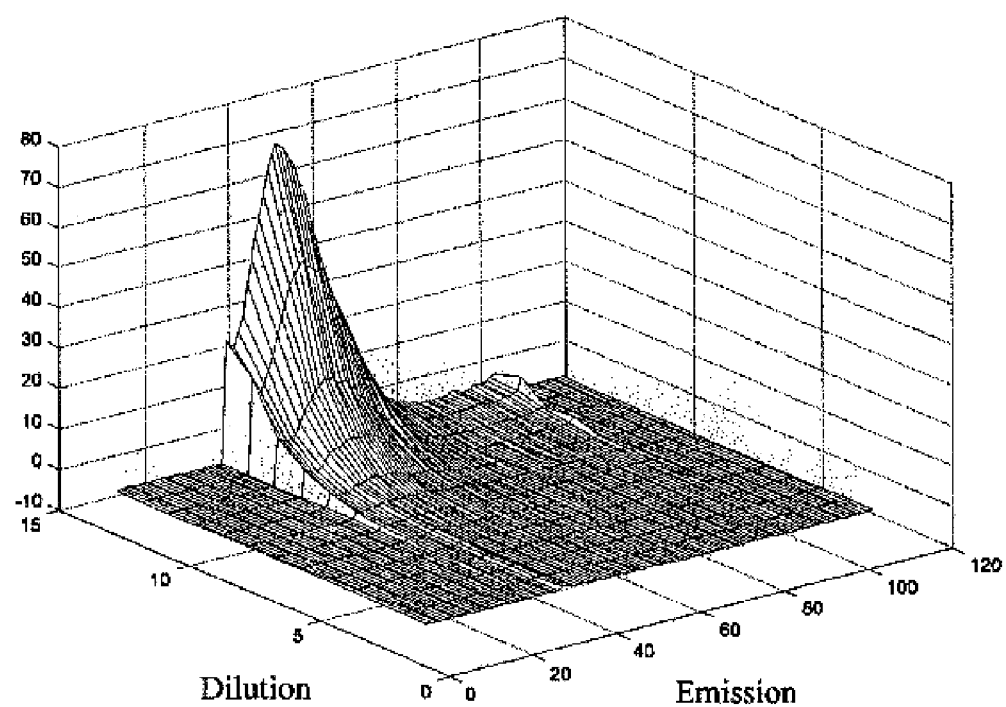

At low excitation wavelengths the signal intensities at first increase with dilution (probably due to quenching) followed by a decrease in signal intensity by further dilution. At high excitation wavelengths a (almost linear) decrease in signal intensity is seen with dilution. This is illustrated in FIGS. 14 and 15.

PCA

A PCA is performed on the mean centered unfolded spectral data. Variables with standard deviation of 0 and variables including missing values (NaNs) are excluded. Systematic score patterns are seen for up to 5 to 6 PCs and FIG. 16 shows the scores for 1 to 4 PCs. Variance explained is 79.38%, 16.32%, 2.60%, 1.45% and 0.24% for the first 5 PCs, respectively.

Experiment 2: Dilution of Blood Samples Measured in Transmission Mode

Raw Data

Figure 17A:
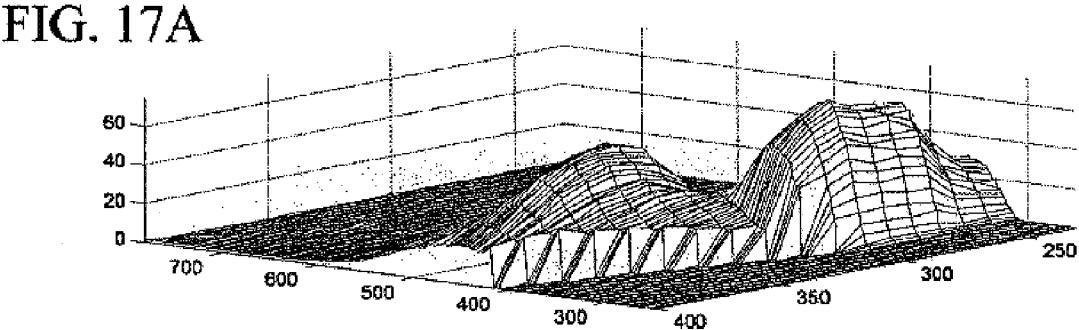
Figure 17B:
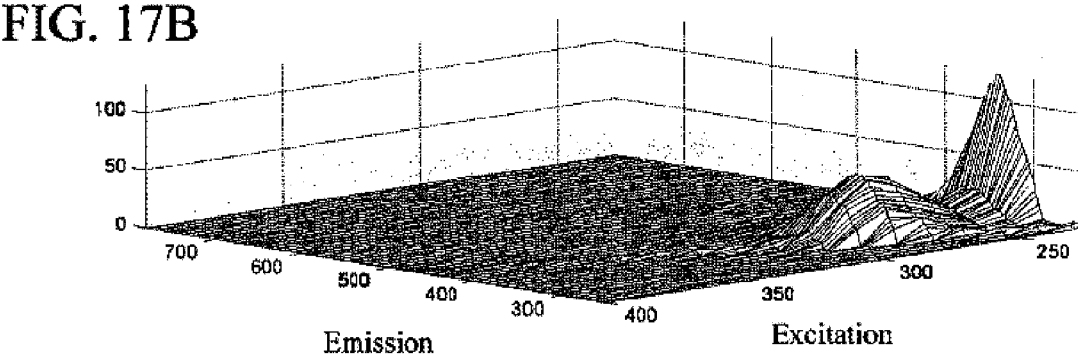

In FIG. 17 examples of transmission fluorescence spectra of an undiluted sample and the same sample diluted 1:5000 are shown. Again, very different spectral signals both with respect to intensity and shape are obtained for the two samples.

At low excitation wavelengths the signal intensities at first increase with dilution (probably due to quenching) followed by a decrease in signal intensity by further dilution. At high excitation wavelengths a (almost linear) decrease in signal intensity is seen with dilution. This is illustrated in FIGS. 18 and 19.

PCA

A PCA is performed on the mean centered unfolded spectral data. Variables with standard deviation of 0 and variables including missing values (NaNs) are excluded. Systematic score patterns are seen for up to 5 to 6 PCs as for front face mode and FIG. 20 shows the scores for 1 to 4 PCs. Variance explained is 85.43%, 11.33%, 1.91%, 0.99% and 0.30% for the first 5 PCs, respectively.

PLS Models

Mean centered PLS models with fluorescence spectra as the independent variables and the dilution factor as the dependent variable are developed for both front face and transmission mode measurements.

It is observed that there is a linear relationship from dilution factor 1:25 to 1:5000 for front face and for 1:50 to 1:5000. It seems that the relationship is non-linear below these dilutions factors. PLS modelling was also tested with auto scaled data to give the high excitation wavelengths more influence. Equal results were obtained although the linear range of the models could be expanded to approx. 1:10. PLS modelling was also tested with log(dilution factor) and nice linear models over the whole range were obtained. Only the undiluted sample seemed to deviate a little.

Experiment 3: Effect of pH & Dilution on the Measured Spectra

PCA

PCA is performed on each of the data sets recorded in transmission and front face mode. A score plot from a PCA on all samples is shown in FIG. 23.

Figure 24:
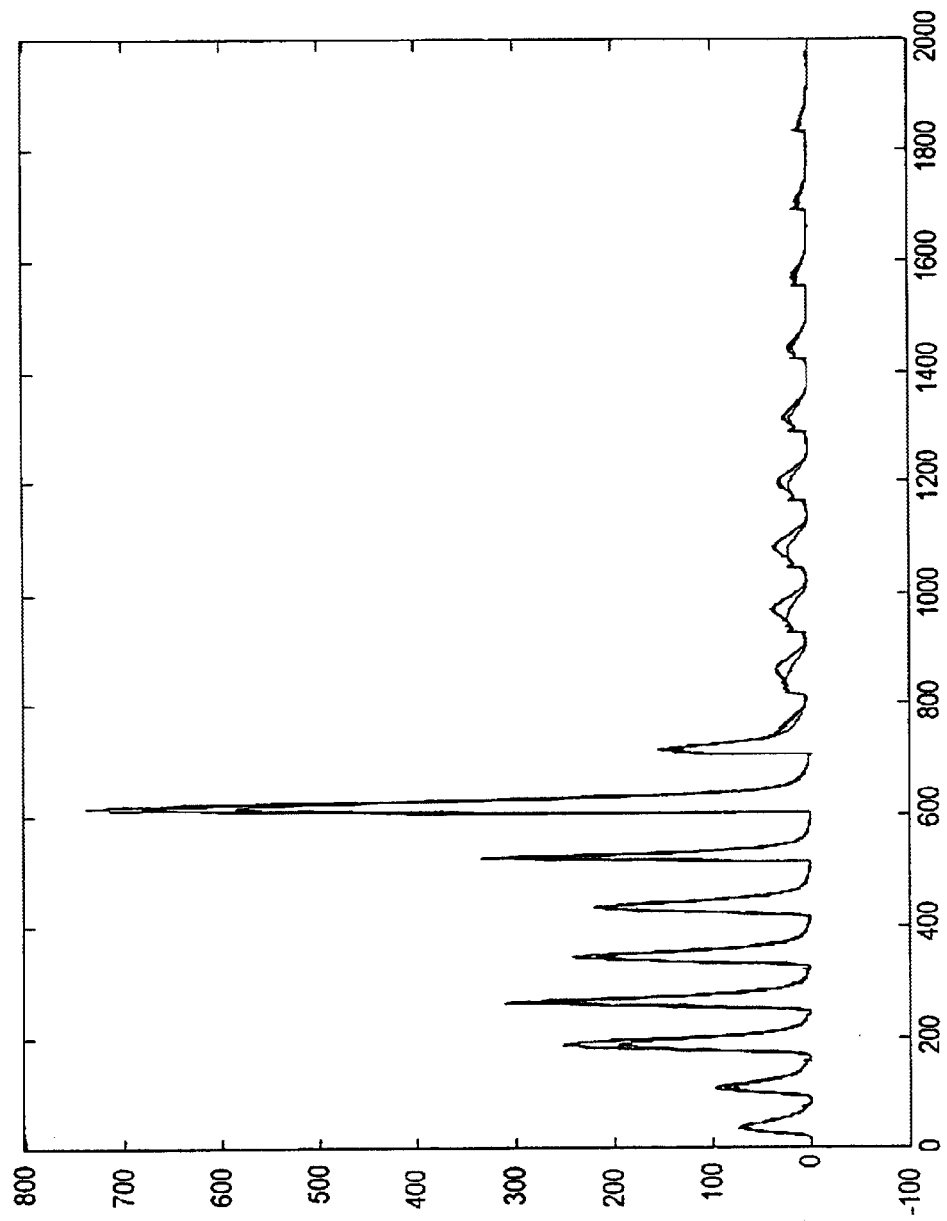

No huge differences are seen with respect to pH levels, see also FIG. 24.

Conclusions

It is important to measure at least two (or even better three or four) different dilutions of the blood plasma samples: the undiluted sample and the same sample diluted 1:2 in front face and diluted 1:200/1:100 in transmission. Not surprisingly, front face intensities are higher for samples measured at no or low dilution factors, while the opposite holds for samples with high dilution factors. Note, that it is possible to measure in transmission mode on the undiluted sample. The tested pH levels do not seem have large effects on the measured spectral shapes or intensities.

REFERENCE LIST

1. Alsberg B K, Goodacre R, Rowland J J, Kell D B, Classification of pyrolysis mass spectra by fuzzy multivariate rule induction-comparison with regression, k-nearest neighbour, neural and decision-tree methods, Analytica Chimica Acta, 1997, 348, 389–407.
2. Bartholomew D J, The foundation of factor analysis, Biometrika, 1984, 71, 221–232.
3. Björkström A, Sundberg R, A generalized view on continuum regression, Scandinavian Journal of Statistics, 1999, 26, 17–30.

4. Bro R. PARAFAC. Tutorial and applications, Chemom Intell Lab Syst, 1997, 38, 149–171.
5. Bro R, Multiway calibration. Multi-linear PLS, Journal of Chemometrics, 1996, 10, 47–61.
6. Bro R, Multi-way Analysis in the Food Industry. Models, Algorithms, and Applications. Ph.D. thesis, University of Amsterdam (NL), 1998,
7. Bro R, Exploratory study of sugar production using fluorescence spectroscopy and multi-way analysis, Chemom Intell Lab Syst, 1999, 46, 133–147.
8. Cheng B, Titterington D M, Neural Networks: A Review from a Statistical Perspective, Statistical Science, 1994, 9, 2–54.
9. de Jong S, Kiers H A L, Principal covariates regression. Part 1. Theory, Chemom Intell Lab Syst, 1992, 14, 155–164.
10. Esbensen K, Wold S, SIMCA, MACUP, SELPLS, GDAM, SPACE & UNFOLD: The way towards regionalized principal components analysis and sub-constrained N-way decomposition—with geological illustrations, Proc Nord Symp Appl Statist, Stavanger, 1983,
11. Faber N M, Buydens L M C, Kateman G, Generalized rank annihilation method. I: Derivation of eigenvalue problems, Journal of Chemometrics, 1994, 8, 147–154.
12. Golub G H, Hansen P C, O'leary D, Tikhonov Regularization and Total Least Squares, SIAM Journal of Numerical Analysis, 1999, 21, 185–194.
13. Grung B, Manne R, Missing values in principal component analysis, Chemom Intell Lab Syst, 1998, 42, 125–139.
14. Indahl U G, Sahni N S, Kirkhus B. Naes T, Multivariate strategies for classification based on NIR—spectra—with application to mayonnaise, Chemom Intell Lab Syst, 1999, 49, 19–31.
15. Jackson J, *A Users Guide to Principal Components*. Wiley & Sons, New York, 1991.
16. Kohonen T, Self-organized formation of topologically correct feature maps, Biological Cybernetics, 1982, 43, 59–69.
17. Kruskal J B, Harshman R A, Lundy M E, Some relationships between Tucker's three-mode factor analysis and PARAFAC/CANDECOMP.1983,
18. Martens H, Nees T. Multivariate calibration. John Wiley & Sons, Chichester, 1989, Martens H, Naes T, Multivariate calibration by data compression, Near Infrared Technology in the Agricultural and Food Industries, (Eds. Williams, P and Norris, K), The american association of cereal chemists, Inc., St. Paul, 1987, 57–87.
19. Naes T, lsaksson T. Some modifications of locally weighted regression (LWR), NIR news, 1994, 5, 8–9.
20. 16. Rajko R, Treatment of model error in calibration by robust and fuzzy procedures, Analytical Letters, 1994, 27, 215–228.
21. 17. Wold S, Dunn W J, III, Multivariate quantitative structure-activity relationships (QSAR): conditions for their applicability, J Chem lnf Comput Sci, 1983, 23, 6–13.
22. Wold S, Cross-validatory estimation of the number of components in factor and principal components models, *Technometrics*, 1978, 20, 397–405.
23. Wold S, Albano C, Dunn W J, III, Edlund U, Esbensen K H, Geladi P, Hellberg S, Johansson E, Lindberg W, Sjöström M, Multivariate data analysis in chemistry, Chemometrics. Mathematics and Statistics in Chemistry, (Ed. Kowalski,B R), D. Reidel Publishing Company, Dordrecht, 1984, 17–95.

What is claimed is:

1. A method of training a classification system for characterising an isolated biological sample with respect to at least one condition, comprising
   a) obtaining an isolated biological sample from an animal wherein said isolated biological sample is selected from body fluids,
      from a tissue sample or a combination thereof, wherein said tissue sample is not associated with said condition(s),
   b) obtaining characterisation information related to each isolated biological sample,
   c) exposing the sample to excitation light within a predetermined range of wavelength,
   d) determining at least one physical parameter of light emitted from the sample,
   e) repeating step a) to d) until the physical parameters of all training samples have been determined,
   f) optionally performing a data handling of the obtained physical parameters obtaining data variables,
   g) optionally performing a multivariate data analysis of the data variables and optionally of characterisation information obtaining model parameters describing the variation of the data variables,
   h) classifying the biological samples into at least two different classes correlated to the characterisation information, obtaining a trained classification system.

2. The method according to claim 1, wherein step g) further comprises selection of latent variables being weighted averages of data variables.

3. The method according to claim 1, wherein the biological sample is selected from blood, serum, plasma, saliva, urine, milk, cerebrospinal fluid, tears, nasal secrete, semen, bile, lymph, sweat and/or faeces.

4. The method according to claim 1, wherein the biological sample is a tissue sample.

5. The method according to claim 4, wherein the tissue sample is a biopsy of tissue selected from muscle, cutis, subcutis, kidney, brain, and liver or a sample of hair or nails.

6. The method according to claim 3, wherein the biological sample is urine, milk, blood, plasma or serum.

7. The method according to claim 1, wherein the wavelength of the excitation light is in the range of from 100 nm to 1000 nm.

8. The method according to claim 7, wherein the wavelength of the excitation light is in the range of from 200 nm to 800 nm.

9. The method according to claim 1, wherein the physical parameter determined is selected from fluorescence intensity, fluorescence lifetime, phosphorescence intensity, phosphorescence lifetime, polarisation, polarisation lifetime, anisotropy, anisotropy lifetime, phase-resolved emission, circularly polarised fluorescence, fluorescence-detected circular dichroism, and any time dependence of the two last mentioned parameters.

10. The method according to claim 1, wherein the spectral distribution of light emitted ranging from 200 nm to 800 nm is generated.

11. The method according to claim 2, wherein the ratio of number of training samples to the expected number of latent variables is at least 5:1.

12. The method according to claim 1, wherein the multivariate data analysis is selected from: Principal component analysis, principal component regression, factor analysis, partial least squares, fuzzy clustering, artificial neural networks, parallel factor analysis, Tucker models, generalised rank annihilation method, locally weighted regression, ridge regression, total least squares, principal covariates regression, Kohonen networks, linear or quadratic discriminant analysis, k-nearest neighbours based on rank-reduced distances, multilinear regression methods, soft independent modelling of class analogies, robustified versions of the above obvious non-linear versions, and combinations thereof.

13. The method according to claim 1, wherein step f) is selected from a one-way matrix of spectral information, a two-way matrix of spectral information, a three-way matrix of spectral information, a four-way matrix of spectral information and, a five-way or higher order matrix of spectral information.

14. The method according to claim 1, wherein at least one other variable is included in the multivariate analysis of step g).

15. The method according to claim 14, wherein the at least one other variable is selected from a pH value of the sample, concentration of various electrolytes in the sample, concentration of any other relevant compound in the sample, temperature, chemical parameters or any other physical property of the sample.

16. The method according to claim 1, wherein at least one other variable related to the animal is included in the multivariate analysis of step g).

17. The method according to claim 16, wherein the at least one other variable is selected from any parameter relating to the bodily or mental condition, hair colour, skin colour, age, sex, geographic origin, affiliation, hereditary background, stress level, medical diagnosis, subjective evaluations or clinical parameters.

18. The method according to claim 1, wherein the sample is pre-treated before subjecting the sample to step c).

19. The method according to claim 18, wherein the pre-treatment comprises adjustment of pH of the sample to a predetermined value.

20. The method according to claim 1, wherein a classification system for diagnostic purposes with relation to heart diseases is obtained.

21. The method according to claim 1, wherein a classification system for diagnostic purposes with relation to abuse of medicine or narcotics is obtained.

22. A diagnostic classification system comprising
   a) a sample domain for comprising a biological sample,
   b) light means for exposing the sample to excitation light in the sample domain,
   c) a detecting means recording at least one physical parameter of light emitted from the sample,
   d) at least one detecting means for measuring at least one other variable of the sample,
   e) optionally computing means for performing data handling of the physical parameters, obtaining data variables,
   f) optionally processing means for providing model parameters from data variables of the sample,
   g) at least one storage means for storing physical parameters, data variables, model parameters, or some combination thereof of the biological sample,
   h) at least one storage means for storing physical parameters, data variables, model parameters, characterisation information, or some combination thereof of a trained classification system,
   i) means for correlating physical parameters, data variables, model parameters, or some combination thereof from the sample with physical parameters, data variables, model parameters, or some combination thereof of the trained system, and
   j) means for displaying at least one characterisation class of a sample.

23. The system according to claim 22, wherein the model parameters are latent variables being weighted averages of the data variables.

24. The system according to claim 22, wherein the biological sample is a liquid sample.

25. The system according to claim 22, wherein the biological sample is a tissue sample.

26. The system according to claim 25, wherein the tissue sample is a biopsy of tissue selected from muscle, cutis, subcutis, kidney, brain, and liver or a sample of hair or nails.

27. The system according to claim 24, wherein the biological sample is urine, milk, blood, plasma or serum.

28. The system according to claim 22, wherein the light means is arranged to emit light having a wavelength in the range of from 100 nm to 1000 nm.

29. The system according to claim 28, wherein the light means is arranged to emit light having a wavelength in the range of from 200 nm to 800 nm.

30. The system according to claim 22, wherein the physical parameter determined is selected from fluorescence intensity, fluorescence lifetime, phosphorescence intensity, phosphorescence lifetime, polarisation, polarisation lifetime, anisotropy, anisotropy lifetime, phase-resolved emission, circularly polarised fluorescence, fluorescence-detected circular dichroism, and any time dependence of the two last mentioned parameters.

31. The system according to claim 22, wherein the detecting means is a photomultiplier, or a scanning camera.

32. The system according to claim 22, being divided into at least a first unit and a second unit, wherein said first unit comprises the parts a) to at least c) of the system, and the second unit comprises the other parts.

33. The system according to claim 22, wherein the at least one other variable is selected from a pH value of the sample, concentration of various electrolytes in the sample, concentration of any other relevant compound in the sample, temperature, chemical parameters or any other physical property of the sample.

34. The system according to claim 22, further including means for entering other variables.

35. The system according to claim 34, wherein the at least one other variable a is selected from any parameter relating to the bodily or mental condition, hair colour, skin colour, age, sex, geographic origin, affiliation, hereditary background, stress level, medical diagnosis, subjective evaluations or clinical parameters.

36. The system according to claim 22, wherein the sample is pre-treated before subjecting the sample to step b).

37. The system according to claim 36, wherein the pre-treatment comprises adjustment of pH of the sample to a predetermined value.

38. The system according to claim 22, being a classification system for diagnostic purposes with relation to heart diseases.

39. The system according to claim 22, being a classification system for diagnostic purposes with relation to abuse of medicine or narcotics.

40. A method for characterising a biological sample of an animal with respect to at least one condition, comprising.
   a) obtaining an isolated biological sample from the animal wherein said biological sample is selected
from body fluids or
from a tissue sample, wherein said tissue sample is not associated with the at least one condition,
b) exposing the sample to excitation light,
c) determining at least one physical parameter of light emitted from the sample,
d) optionally performing data handling of the obtained physical parameters obtaining data variables,
e) storing the physical parameters, data variables, model parameters, or some combination thereof
f) optionally providing model parameters from data variables of the sample,
g) obtaining physical parameters, data variables, model parameters, or some combination thereof from a trained classification system,
h) correlating physical parameters, data variables, model parameters, or some combination thereof from the sample with physical parameters, data variables, model parameters, or some combination thereof of the trained system, and
i) displaying at least one characterisation class of the sample.

41. The method according to claim 40, wherein the model parameters are latent variables being weighted averages of the data variables.

42. The method according to claim 40, wherein the biological sample is selected from blood, serum, plasma, saliva, urine, cerebrospinal fluid, tears, nasal secrete, semen, milk, bile, lymph, sweat, faeces, or some combination thereof.

43. The method according to claim 40, wherein the biological sample is a tissue sample.

44. The method according to claim 40, wherein the tissue sample is a biopsy of tissue selected from muscle, cutis, subcutis, kidney, brain, and liver or a sample of hair of nails.

45. The method according to claim 42, wherein the biological sample is urine, blood, milk, or serum.

46. The method according to claim 40, wherein the wavelength of the excitation light is in the range of from 100 nm to 1000 nm.

47. The method according to claim 40, wherein the wavelength of the excitation light is in the range of from 200 nm to 800 nm.

48. The method according to claim 40, wherein the at least one physical parameter determined is selected from fluorescence intensity, fluorescence lifetime, phosphorescence intensity, phosphorescence lifetime, polarisation, polarisation lifetime, anisotropy, anisotropy lifetime, phase-resolved emission, circularly polarised fluorescence, fluorescence-detected circular dichroism, any time dependence of the last mentioned parameters, or some combination thereof.

49. The method according to claim 40, wherein the spectral distribution of light emitted ranging from 200 nm to 800 nm is generated.

50. The method according to claim 40, wherein the data handling of step d) is selected from a one-way matrix of spectral information, a two-way matrix of spectral information, a three-way matrix of spectral information, a four-way matrix of spectral information and, a five-way or higher order matrix of spectral information.

51. The method according to claim 40, wherein at least one other variable is included as data variables.

52. The method according to claim 51, wherein the at least one other variable a is selected from a pH value of the sample, concentration of various electrolytes in the sample, concentration of any other relevant compound in the sample, temperature, chemical parameters or any other physical property of the sample.

53. The method according to claim 40, wherein at least one other variable related to the animal is included as data variables.

54. The method according to claim 53, wherein the at least one other variable is selected from any parameter relating to the bodily or mental condition, hair colour, skin colour, age, sex, geographic origin, affiliation, hereditary background, stress level, medical, diagnosis, subjective evaluations or clinical parameters.

55. The method according to claim 40, wherein the sample is pre-treated before subjecting the sample to step b).

56. The method according to claim 55, wherein the pre-treatment comprises adjustment of pH of the sample to a predetermined value.

57. The method according to claim 40, wherein the trained classification system is a diagnostic heart disease classification system.

58. The method according to claim 40, wherein the trained classification system is a diagnostic abuse classification system related to abuse of medicine or narcotics.

59. The method of claim 1, wherein said animal is a human.

60. The method of claim 40, wherein said animal is a human.

* * * * *